United States Patent [19]

Callahan et al.

[11] Patent Number: 5,094,244

[45] Date of Patent: Mar. 10, 1992

[54] APPARATUS AND PROCESS FOR DETERMINING SYSTOLIC BLOOD PRESSURE, DIASTOLIC BLOOD PRESSURE, MEAN ARTERIAL BLOOD PRESSURE, PULSE RATE, PULSE WAVE SHAPE, RESPIRATORY PATTERN, AND RESPIRATORY RATE

[75] Inventors: Wayne Callahan, Brentwood, Tenn.; Walter Harriman, Sanford, N.C.

[73] Assignee: Health Monitors, Inc., Brentwood, Tenn.

[21] Appl. No.: 398,488

[22] Filed: Aug. 25, 1989

[51] Int. Cl.$^5$ ............................................. A61B 5/02
[52] U.S. Cl. ................................. 128/677; 128/686
[58] Field of Search .............. 128/677, 679, 681, 686

[56] References Cited

U.S. PATENT DOCUMENTS

| | | | |
|---|---|---|---|
| 3,527,204 | 9/1970 | Lem et al. | 128/686 |
| 3,752,148 | 8/1973 | Schmolzbach | 128/686 |
| 3,903,872 | 9/1975 | Link | 128/681 |
| 3,935,984 | 2/1976 | Lichowsky et al. | 128/686 |
| 4,009,709 | 3/1977 | Link et al. | 128/681 |
| 4,572,205 | 2/1986 | Sjönell | 128/686 |
| 4,651,747 | 3/1987 | Link | 128/681 |
| 4,664,126 | 5/1987 | Link | 128/681 |
| 4,729,382 | 3/1988 | Schaffer et al. | 128/679 |
| 4,862,895 | 9/1989 | Yamasawa et al. | 128/686 X |
| 4,867,170 | 9/1989 | Tabahashi et al. | 128/677 |

FOREIGN PATENT DOCUMENTS 2640682  3/1977  Fed. Rep. of Germany ........ 128/660.02

OTHER PUBLICATIONS

Close et al., "Finger Systolic Pressure: Its Use in Screening for Hypertension and Monitoring", 9/27/1986, British Medical Journal, vol. 293, pp. 775–778.

Nakayama et al., "Noninvasive Measurements of Digital Arterial Pressure and Compliance in Man", pp. H169–H178.

Ludbrook et al., "Measurement of Blood Pressure, Blood Flow and Resistance to Blood Flow in the Systemic Circulation", 8 pages.

Patla et al., "Mvoelectric Signal as a Quantitative Measure of Muscle Mechanical Output", Jan. 1977, Medical & Biological Engineering & Computing, pp. 6–9.

Forster et al., "Oscillometric Determination of Diastolic, Mean and Systolic Blood Pressure–A Numberical Model", Nov. 1986, vol. 108, Journal of Biomechanical Engineering, pp. 359–364.

Johnson et al., "Automatic Blood Pressure Monitors", 1985, The Association of Anaesthetsts of Gt Britain and Ireland, pp. 471–479.

L. A. Geddes, "Blood Pressure Noninvasive Measurement", 1982, pp. 66–91.

L. A. Geddes, "Blood Pressure and its Direct Measurement", 1982, pp. 18–51.

*Primary Examiner*—Francis Jaworski
*Attorney, Agent, or Firm*—Cushman, Darby & Cushman

[57] ABSTRACT

An apparatus and process for automatically measuring systolic, diastolic and mean arterial blood pressure. Two cuffs, one located closer to the heart (proximal) than the second (distal), are provided. Each cuff is attached to a small manifold which has three ports. One port is connected to the cuff, one port is connected to a pressure sensor, and the last port is connected to a valve to a high pressure air source. Throughout blood pressure monitoring, a constant mass of air is maintained within the cuff by inflating the cuff and closing the cuff valve. The sensors are connected to a microcomputer so that the static pressure component and the dynamic pressure component of cuff pressure can be stored and plotted. Mean arterial pressure is read from both distal and proximal cuff sensors. Diastolic blood pressure is determined by recording the proximal static cuff pressure at which a maximum dynamic distal amplitude is observed. Systolic blood pressure is determined by recording the proximal static pressure at which a minimum dynamic distal amplitude is observed.

25 Claims, 17 Drawing Sheets

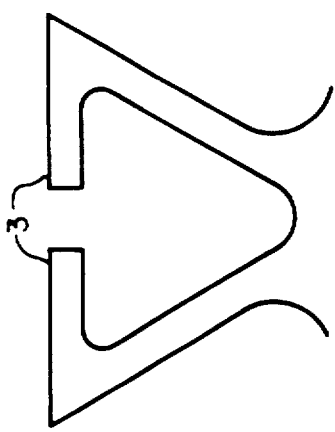
FIG. IA
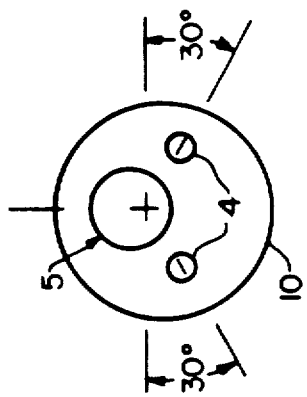
FIG. IB
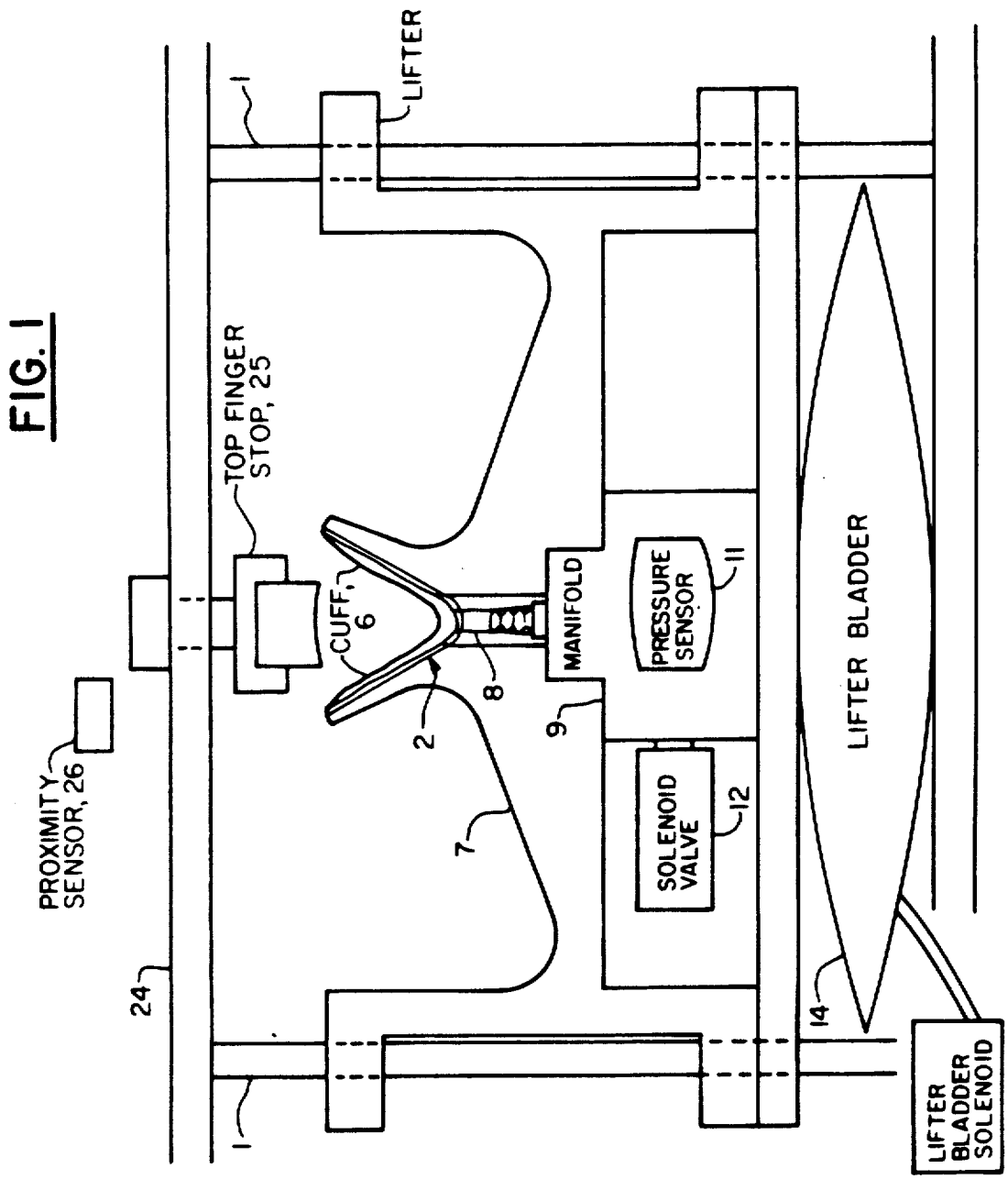
FIG. I

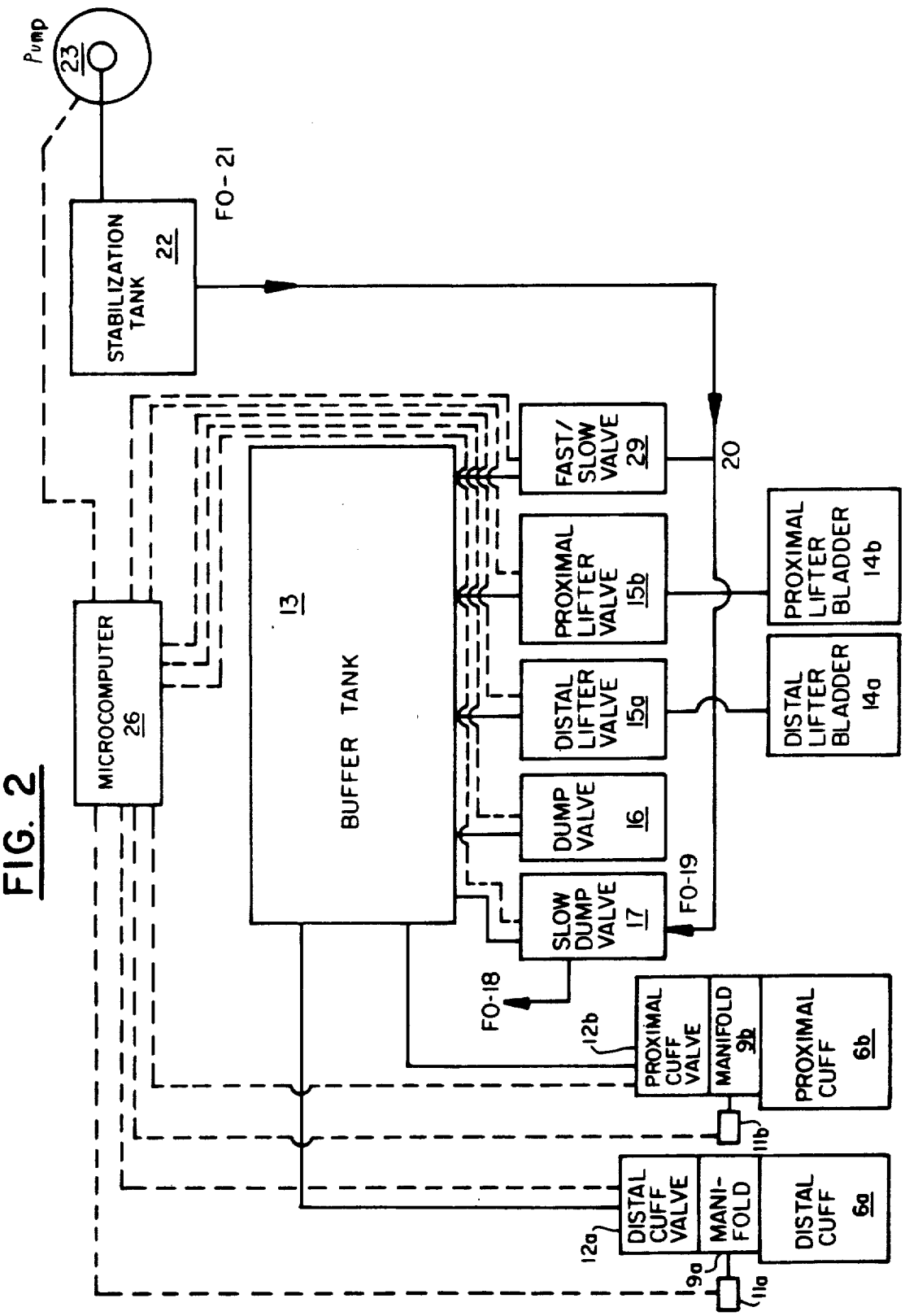

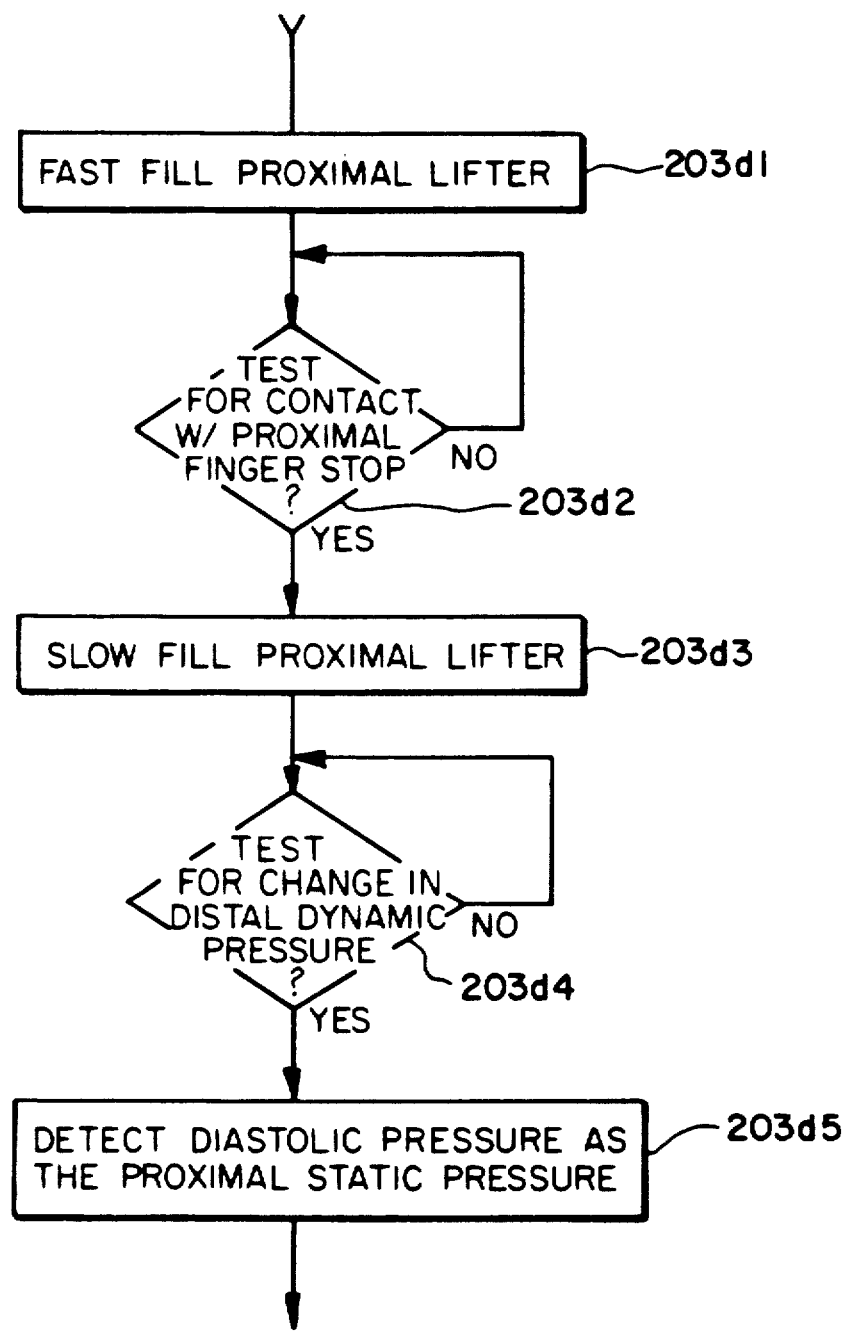

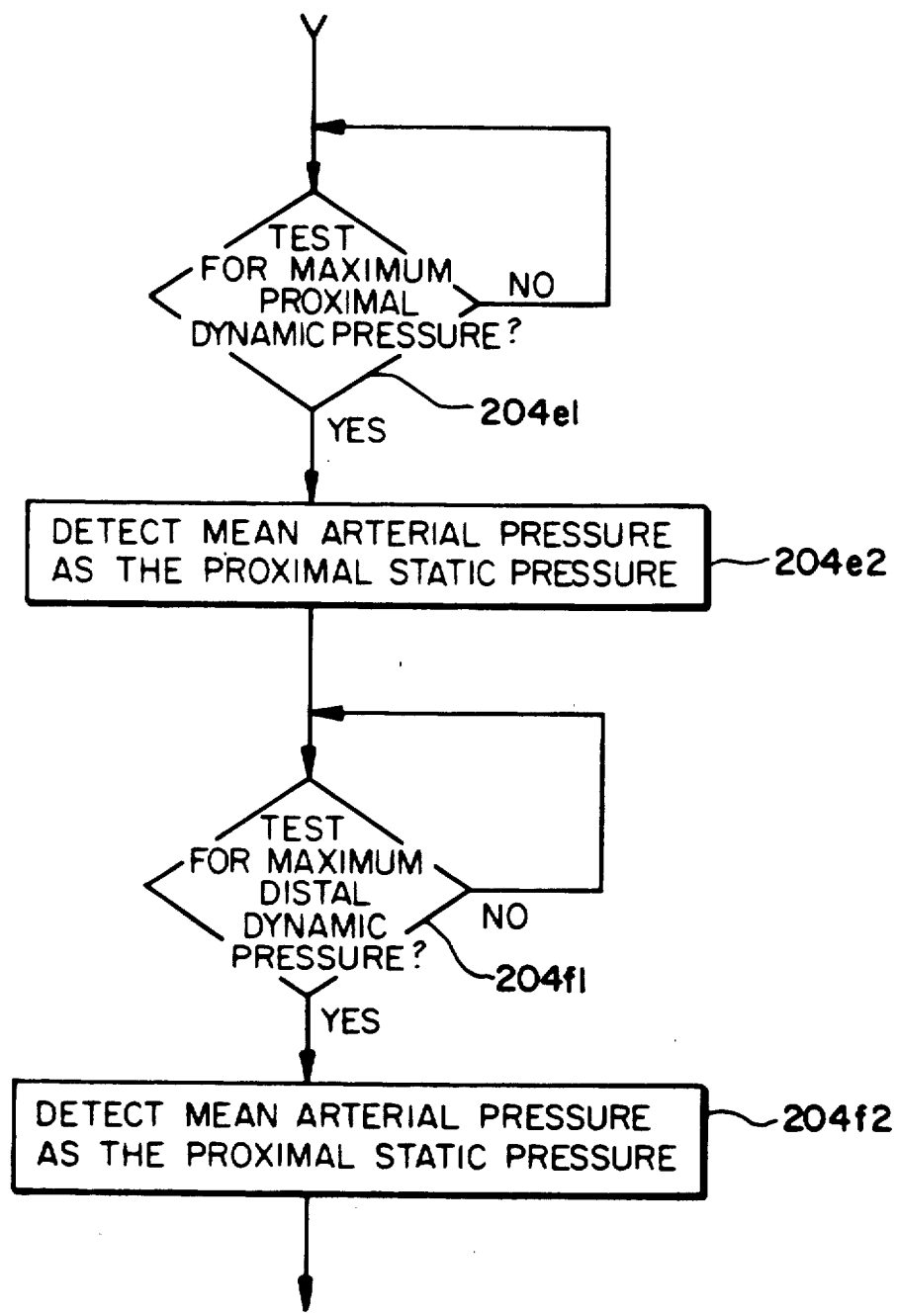

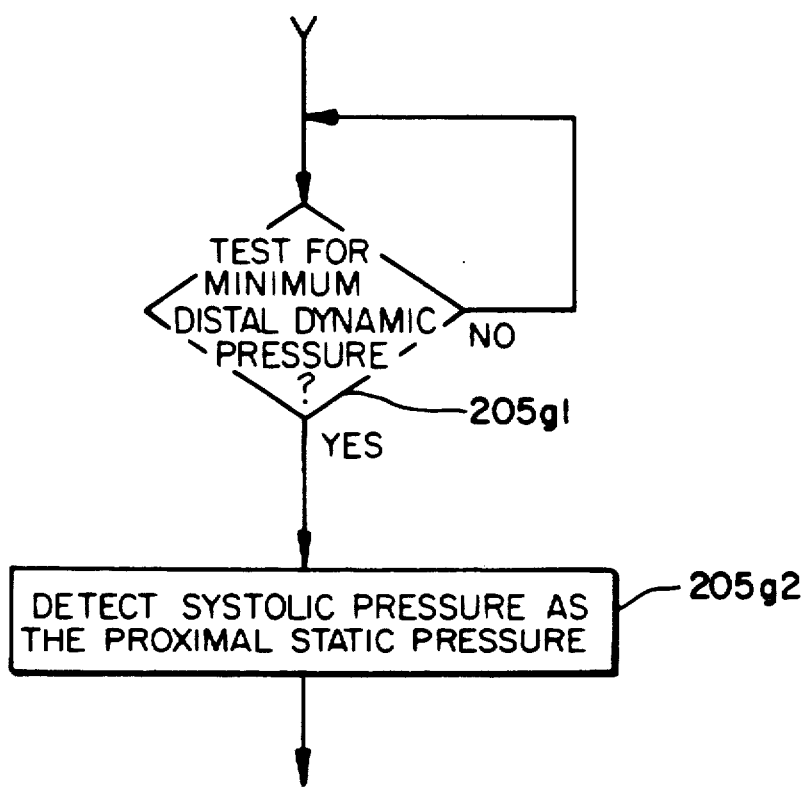

JUST PRIOR TO DIASTOLIC PRESSURE

JUST AFTER DIASTOLIC PRESSURE

ARTERIAL PRESSURE ABOVE DIASTOLIC

MEAN ARTERIAL PRESSURE AND MAXIMUM DEFLECTION

ABOVE MEAN ARTERIAL PRESSURE

SYSTOLIC PRESSURE

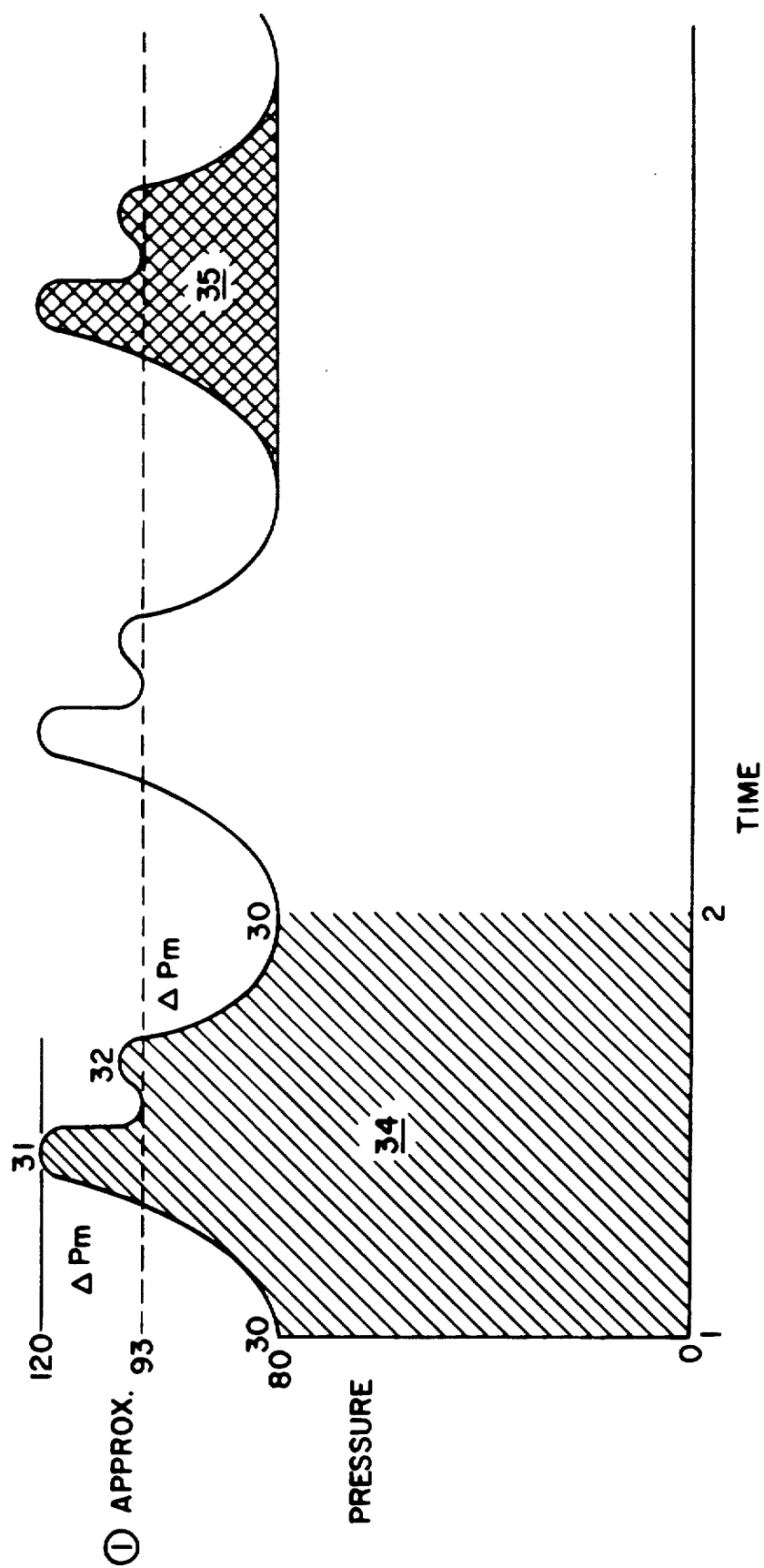

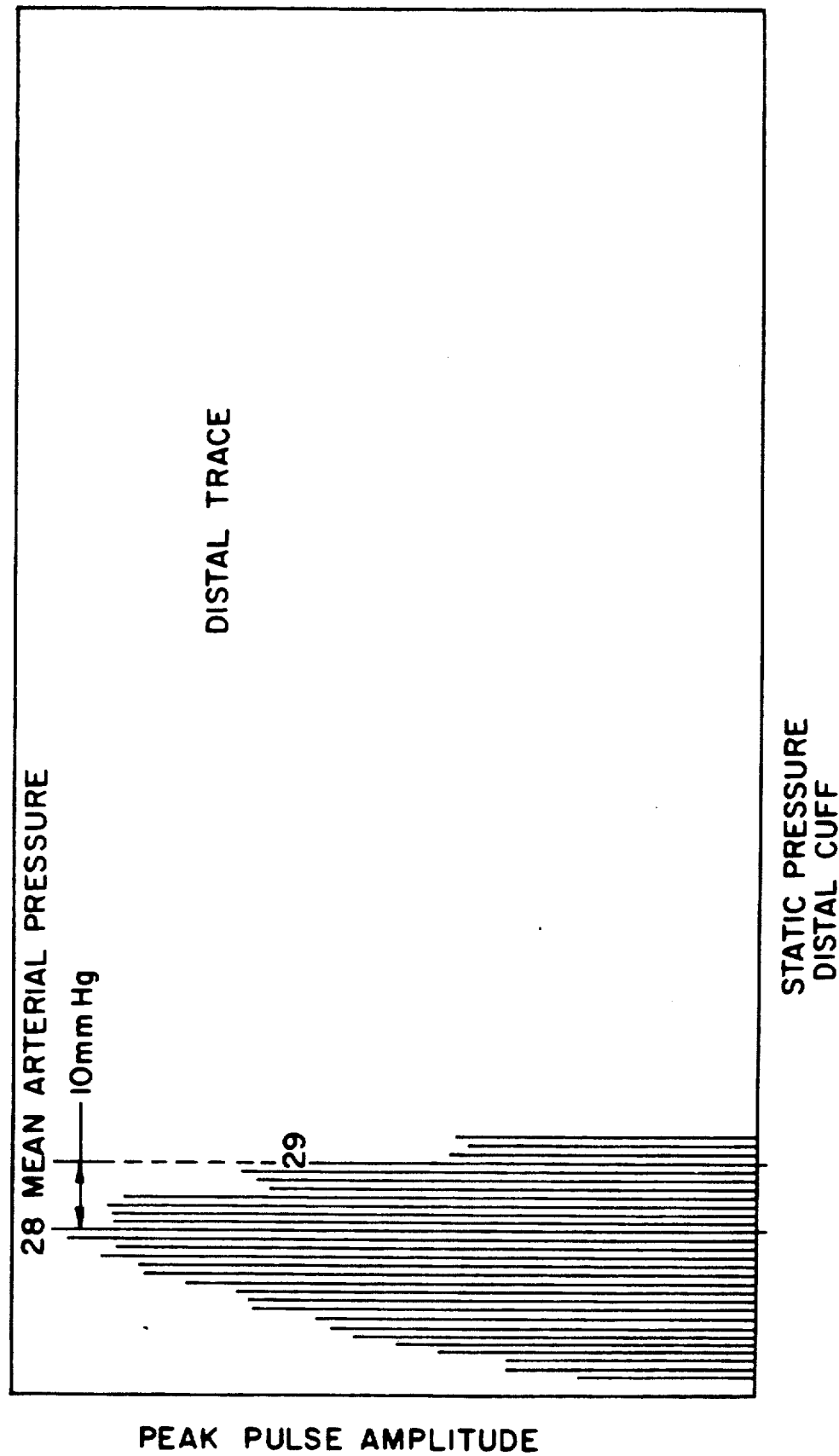

FIG. 5c

K = relationship between the systolic, diastolic and mean arterial pressure.

S = systolic pressure = peak point of figure 3

D = Diastolic Pressure = minimum point of shaded area (figure 3, curve 3)

MAP = Mean Arterial Pressure

ES-D = Sum of the area under the pulse curve where a horizontal line is drawn at the diastolic pressure (figure 3, curve 3) and the area summed is the pulse amplitude minus the diastolic pressure.

T2 = Time at the end of a pulse cycle.

T1 = Time of the beginning of a pulse cycle.

$$K = \frac{MAP-D}{S-D}$$

Note: ES-D, S, D are all in electrical voltages and are relative values. However, each variable is calibrated to the same voltage scale.

$$MAP = \frac{Ap}{T2-T1}$$

Where: MAP = Mean arterial Pressure
Ap = Sum area under the pressure curve (figure 3, curve 1)
T2 = Time at the end of the cycle
T1 = Time at the beginning of the cycle

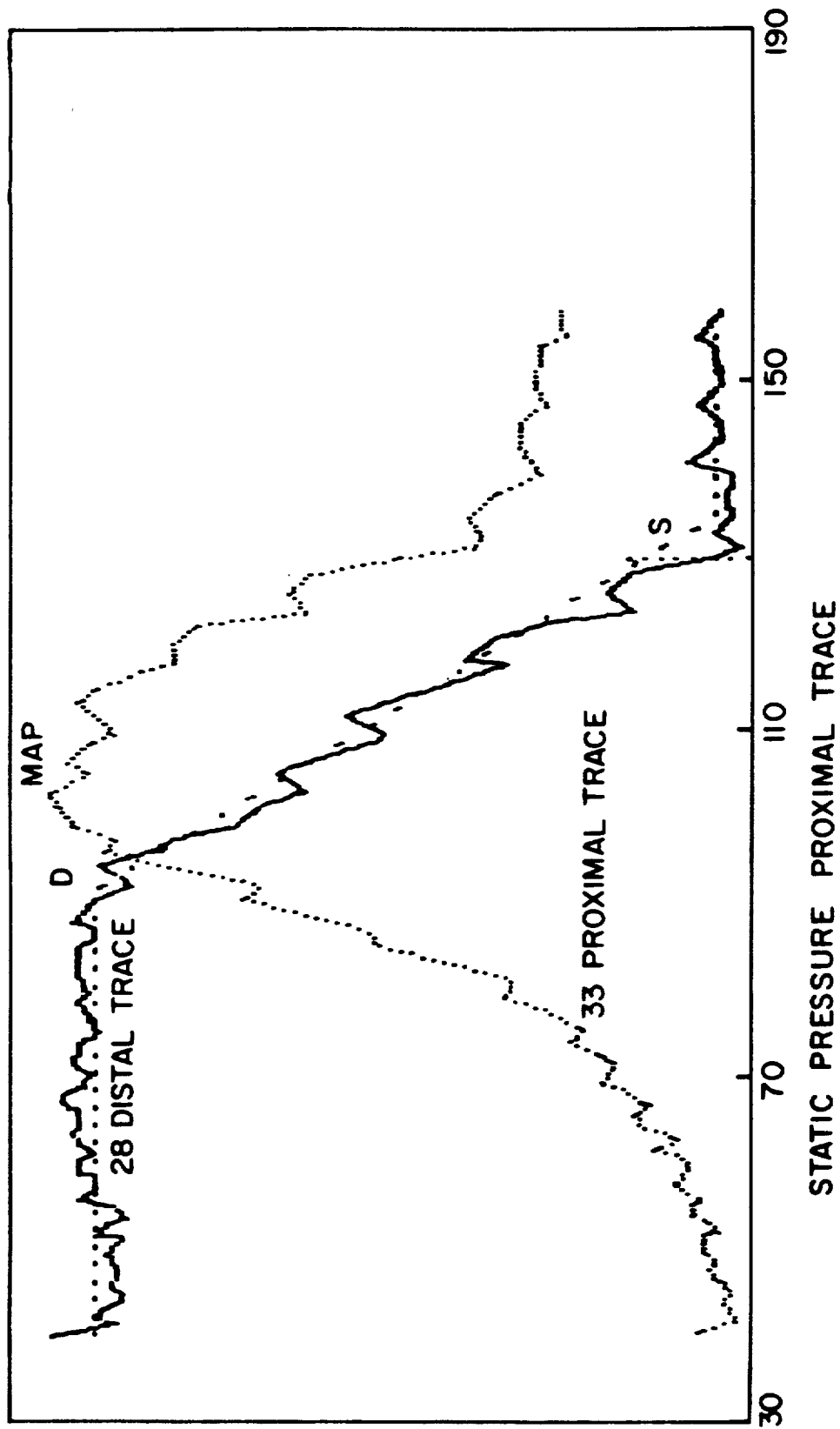

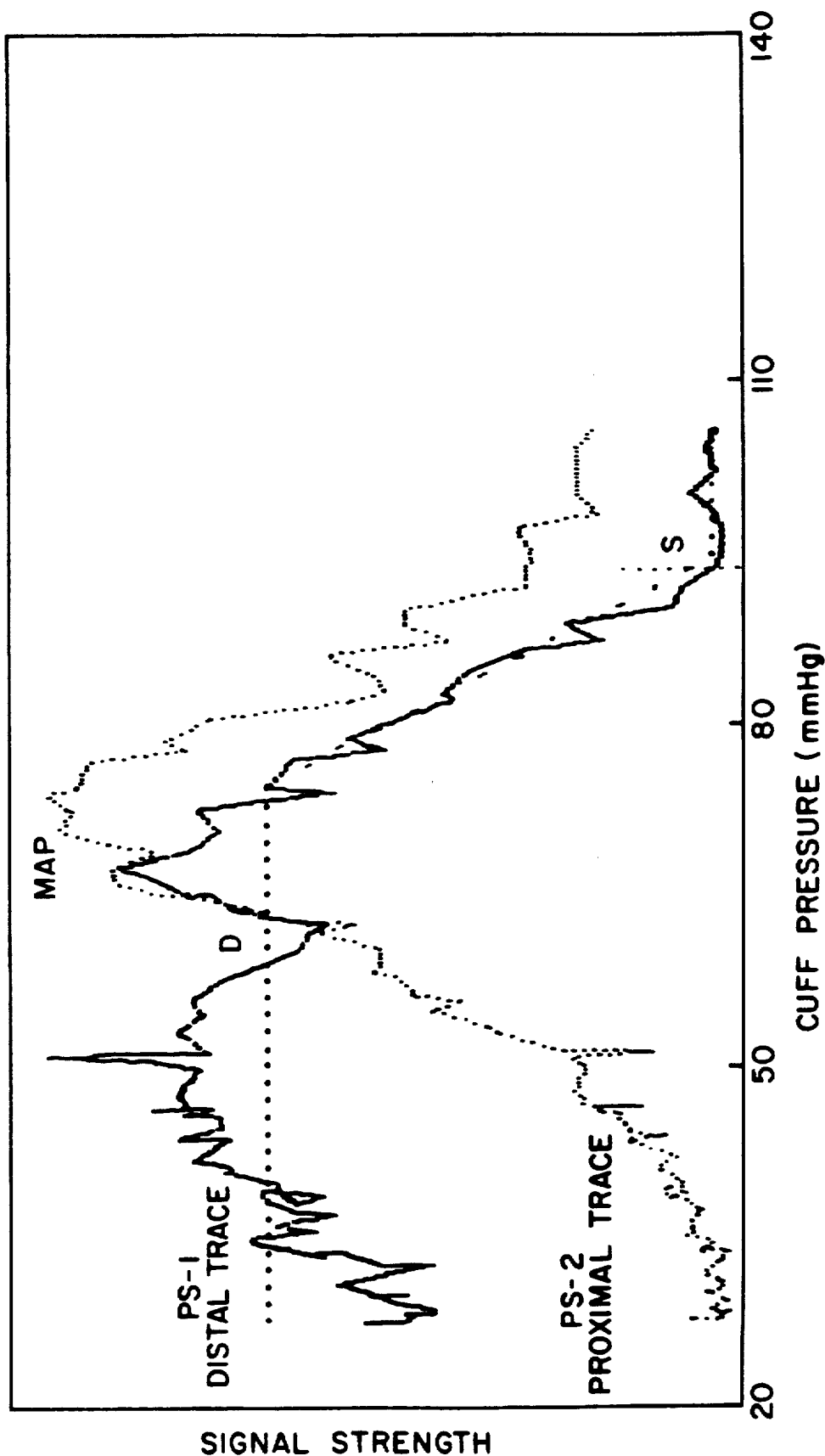

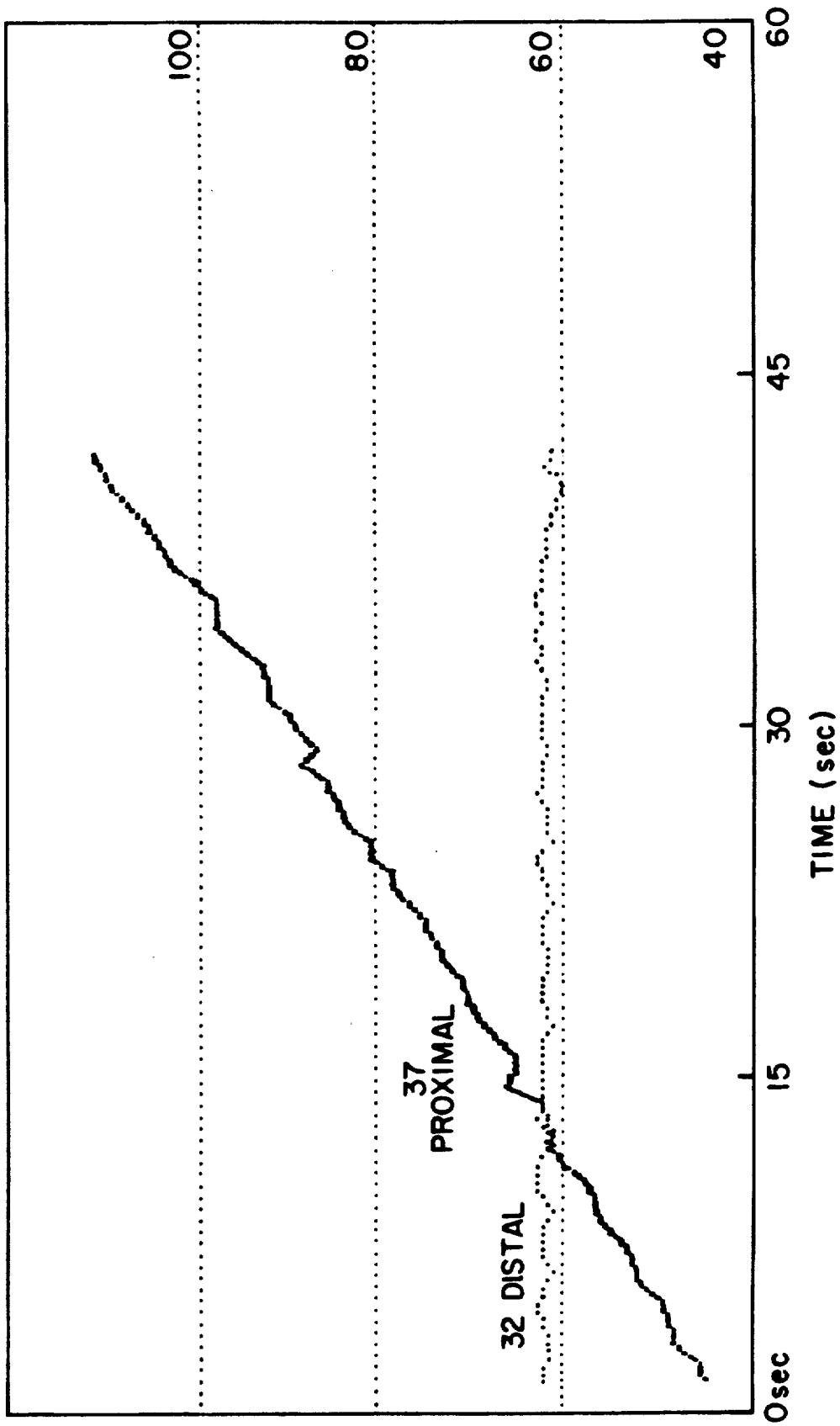

APPARATUS AND PROCESS FOR DETERMINING SYSTOLIC BLOOD PRESSURE, DIASTOLIC BLOOD PRESSURE, MEAN ARTERIAL BLOOD PRESSURE, PULSE RATE, PULSE WAVE SHAPE, RESPIRATORY PATTERN, AND RESPIRATORY RATE

FIELD OF THE INVENTION

This invention relates to the automatic, non-invasive measurement of blood pressure and vital signs through the use of an oscillometric method. Specifically, it relates to a monitor capable of measuring blood pressure, pulse, and respiration rate through the finger.

BACKGROUND OF THE INVENTION

The measurement of blood pressure is an important tool for the medical professional. The term "blood pressure" is a relative term whose precise meaning depends very much on the method used. Blood pressure is the force exerted by the blood against the inner walls of the blood vessels. It is determined by the flow of blood and the resistance to that flow.

Blood pressure is comprised of three parts: the systolic, diastolic, and mean blood pressure. Systolic pressure is the maximum arterial pressure. Diastolic is the minimum arterial pressure. Mean blood pressure is the static pressure that is equivalent to an average pressure. It is found by dividing the area under a single pulse wave by the width of the pulse.

The aortic pressure pulse rises abruptly with aortic ejection and then falls smoothly to the point of the dicrotic notch. The dicrotic notch is attributed to a reflected wave from the recoil of the blood column against the closed aortic valve.

There are several factors that influence arterial blood pressure. They are cardiac output, elastic recoil of the aorta and large arteries, peripheral resistance, volume of blood in the arterial system and viscosity of the blood. Changes in any of the five factors alter either systolic pressure, diastolic pressure, or both pressures.

Devices to measure blood pressure are classified as either direct or indirect. Devices utilizing direct methods all include introducing a pressure sensing element into the blood stream. Because direct methods are invasive, devices utilizing direct methods of measuring blood pressure are impractical for routine clinical examination. Unfortunately, such devices also require a high level of technical skill for the operator. Accordingly, a number of devices utilizing non-invasive indirect methods have been developed. Even though these devices only provide approximate values for intravascular pressure, they are used extensively because physicians need to make routine measurements of blood pressure.

Sphygmomanometry is perhaps the most common type of indirect blood pressure measurement. Sphygmomanometry involves the arrest of flow down an axial artery by the application of a pneumatic cuff. The pressure inside the cuff is manometrically registered. The cuff should meet basic design requirements. Good friction contact is maintained between the cuff and the skin to aid in the constraint of longitudinal tissue motion. The cuff is wide enough to transmit pressure to the artery and the cuff bladder completely encircles the arm.

With sphygmomanometry there must be a means for detecting cessation and onset of blood flow past the cuff as it is inflated or deflated. Monitoring the distal pulse with the finger is one such means. This is, however, insensitive and subjective. Accordingly, more sensitive and objective methods including microphone-amplifier recording, visible capillary refilling or pulsation, plethysmographic pulsation detection, and mercury-in-rubber pulsation detection have been tested. Most notably, auscultation, transcutaneous ultrasonic detection of blood flow, transcutaneous ultrasonic detection of arterial wall movement, and oscillometric pulsation detection are used.

There are two principal ultrasonic methods used in measuring blood pressure. Both methods, however, use a cuff which encircles the limb. In one method, motion of the arterial wall is sensed. In the other, the flow of the blood itself is measured using a Doppler blood flow meter.

Because the walls of the artery beneath an occluding cuff experience a characteristic motion during deflation, it is possible to identify these movements with the first method of ultrasound detection. Two small piezoelectric elements are used. One emits ultrasound and the other detects the ultrasonic echo reflected from the underlying artery. As cuff pressure passes systolic and diastolic pressure, characteristic transitions in the ultrasonic signal are detected.

With the other ultrasonic method, a Doppler blood-flow transducer is placed on the skin over an artery distal to the cuff. When the artery is open, the pulsatile Doppler flow signal is heard or recorded graphically. When the artery is occluded by the cuff, the flow signal disappears. Systolic pressure is read on the first appearance of flow when cuff pressure is decreased During cuff deflation.

The flush method uses an elastic bandage and a limb-encircling cuff. Starting from the tip of the extremity and proceeding to the trunk, a limb is wrapped with a tight elastic bandage such that all the blood is squeezed from the limb. A cuff is then applied just above the trunk end of the bandage and inflated to a high pressure. The bandage is then removed. The opposite undrained limb is then placed beside the blanched member and both are examined in a bright light. Cuff pressure is reduced slowly, and as it passes systolic pressure, blood enters the member and it flushes red. At that particular instant, cuff pressure is read as systolic. There is no indication when cuff pressure is at diastolic pressure or at mean pressure.

Auscultation is listening to sounds that occur within the body. These sounds are known as the Korotkoff sounds in honor of the Russian physician who first proposed the method in 1905. To obtain systolic and diastolic pressure with the auscultatory method, the brachial artery is located and the receiver of a stethoscope placed over it. Cuff pressure is then quickly raised to a point well above systolic pressure. Cuff pressure is then reduced slowly while the observer listens to the arterial sounds. As cuff pressure falls below systolic pressure, a spurt of blood passes under the cuff and a sound is heard in the stethoscope. The cuff pressure at which this sound occurs indicates the systolic pressure. As cuff pressure continues to fall, the sounds become louder, then softer, then very loud, then they become muffled and disappear. Most physicians read the point where the sound disappears as diastolic pressure. However, if the sounds continue to an abnormally low point, physicians use the point where the sound becomes muffled.

In the oscillometric method, variations in amplitude of the blood pressure oscillations are used to identify systolic and mean pressures. There are two components to pressure in a cuff, a static pressure component and a dynamic component. The static component is due to the pressure exerted by the cuff on the limb of body. The dynamic component is due to the pulsation of blood pushing on the cuff. When utilizing the oscillometric method, it is necessary to employ some form of amplification to monitor the small changes in the amplitude of the dynamic component.

In the oscillometric method, cuff pressure is first raised quickly to a point well above systolic pressure where the cuff completely occludes the underlying artery throughout the cardiac cycle. Even though the artery is completely occluded, blood pulsates against the upper edge of the cuff which nevertheless results in small amplitude oscillations on a cuff pressure indicator.

Cuff pressure is then reduced slowly. When cuff pressure falls below systolic pressure, a spurt of blood flows in the artery and the cuff pressure oscillations become larger. As the cuff pressure is further reduced, the oscillations reach a maximum. This maximum corresponds to the maximum change in artery wall dimensions when the heart opens the artery and when the cuff forces the artery closed again on each heart stroke. A further decrease in cuff pressure, therefore, results in a more continuously open artery and the amplitude of the dynamic cuff pressure decreases. The point where amplitude oscillations begin to increase is the point at which systolic pressure is read. The point of maximum oscillation is the mean arterial pressure.

There is, however, no obvious change in cuff pressure oscillation when cuff pressure passes diastolic pressure. Because of this, some physicians have selected diastolic pressure to be the cuff pressure when the oscillations attain a preselected ratio of the maximum amplitude. The ratio is usually chosen to be around 0.8. It has also been assumed that diastolic blood pressure can be obtained from cuff pressure at the point of medium cuff-pressure perturbation.

The methods described above are all manual. These methods all require someone listening and watching to detect the blood pressure. Accordingly, automatic devices capable of reading blood pressure have been developed. The advantages of automatic monitors include ease of use, lower skill level needed by operator, and the elimination of human error in listening for sounds. Automatic, non-invasive blood pressure monitors of this type work either by auscultation or oscillotonometry.

Monitors using auscultation have been available for a number of years.

The first automatic oscillotonometer, on the other hand, was described by Yelderman and Ream in 1977. It consisted of a limb cuff inflated above systolic pressure. Transducers then sensed changes in cuff pressure as the cuff slowly deflated. The first pressure impulse was recorded as systolic pressure; the lowest cuff pressure at which oscillations were maximum was recorded as mean pressure; and the last recorded beat was taken as diastolic pressure. A microprocessor controlled the frequency of recordings and displayed the measurements. The device also included circuits capable of rejecting artifacts produced by patient movement or extraneous pressure on the cuff. Monitors of this type are commercially available.

U.S. Pat. No. 3,903,872 issued to Link in 1975 discloses a single arm cuff for detecting systolic and diastolic blood pressure. The method operates on the principle that pressure applied adjacent to a blood vessel can be plotted against a time derivative of the observed cuff pressure.

U.S. Pat. No. 4,009,709 issued to Link et al. in 1977 discloses a method for detecting systolic pressure. The method uses a conventional arm cuff and an appropriate sensing device to determine the maximum peak pulse amplitude. The systolic pressure is read when the pressure on the cuff is increased until the peak pulse amplitude reading is one half the maximum value.

U.S. Pat. No. 4,651,747 and U.S. Pat. No. 4,664,126 issued to Link in 1987 disclose using a waveform to determine systolic and diastolic pressure. The systolic pressure is determined using the pressure where one-half the maximum pulse amplitude occurs. The diastolic pressure is determined using the slope of the diastolic portion of the pulse curve. Link further shows a method to calculate the area under the curve to obtain the mean arterial pressure.

U.S. Pat. No. 4,729,382 issued to Schaffer et al in 1988 discloses using a two cuff method. The device includes a pressure differential sensor on each cuff and a third sensor to read the static pressure on the proximal cuff. The cuffs are inflated above the point where the second cuff (proximal cuff) occludes blood flow. The sensor in the first cuff (distal cuff) senses no arterially induced pressure pulsation amplitudes. Then deflation begins in both cuffs. When the first cuff detects a pulse, the static pressure sensor connected to the second cuff (proximal cuff) is read to record the systolic pressure. The diastolic pressure is read when the signal on the second cuff (proximal cuff) reaches a steady state.

SUMMARY OF THE INVENTION

The invention comprises an apparatus and process for automatically measuring physiological conditions such as systolic blood pressure, diastolic blood pressure, mean arterial blood pressure, pulse rate, pulse wave shape, respiratory pattern, and respiratory rate. One embodiment of the invention uses two cuffs for affecting blood flow in a limb of the body to be monitored. One of the cuffs, the proximal cuff, is located on the limb of the body at a location proximate to the heart. The other cuff, the distal cuff, is located on the same limb at a location more distant from the heart.

Each cuff also incorporates a pressure sensor and a valve. The pressure sensor detects both the static component of the blood pressure and the dynamic component of the blood pressure by detecting the pressure the cuff exerts on the limb. The valve lets air in and out of the cuff. The pressure with which a cuff presses on the limb is further increased by inflating a bladder beneath the cuff. The inflating bladder presses a lifter against the cuff and the cuff in turn presses against the limb of the body. A microcomputer controls inflating the bladders and monitoring the sensors.

When blood pressure is to be monitored, each cuff is inflated with a given mass of air. The pressure with which the distal cuff presses against the limb is then increased by inflating distal bladder until the maximum dynamic change in cuff pressure is sensed.

When the static distal cuff pressure approximates the cuff pressure for maximum dynamic signal amplitude, several blood pressure pulse wave shapes are stored. The microcomputer then uses this data to determine mean arterial blood pressure, the pulse rate, and the respiratory rate.

The pressure with which the proximal cuff presses against the limb is then increased. Diastolic pressure is sensed when the amplitude of the dynamic distal cuff pressure amplitude decreases.

As the static pressure of the proximal cuff increases further, a maximum dynamic proximal cuff pressure amplitude is detected. The static proximal cuff pressure at which this occurs is recorded as the mean arterial blood pressure.

The pressure of the proximal cuff then continues to increase. Systolic blood pressure is sensed when the distal dynamic cuff pressure amplitude falls to a minimum steady state value.

BRIEF DESCRIPTION OF THE DRAWINGS

FIG. 1 is a diagram of one of the two bladder-lifter-sensor-cuff-stop assemblies of the present invention.

FIG. 1A represents an alternative embodiment of cuff support to that shown in FIG. 1.

FIG. 1B represents internal anatomic relationships in a cross-section of a finger.

FIG. 2 is functional block diagram of the present invention.

FIG. 2b is a flowchart of the Inflate Cuffs Process of the general flowchart of FIG. 2a.

FIG. 2c is a flowchart of the Set Distal Dynamic Amplitude Process of the general flowchart of FIG. 2a.

FIG. 2d is a flowchart of the Detect Diastolic Pressure Process of the general flowchart of FIG. 2a.

FIG. 2f is a flowchart of the Detect Mean Arterial Pressure Process of the general flowchart of FIG. 2a as used in method three.

FIG. 2g is a flowchart of the Detect Systolic Pressure Process of the general flowchart of FIG. 2a.

FIG. 4-a depicts the artery wall not changing dimensions at and below diastolic pressure being applied by the cuff.

FIG. 4-b depicts a slight change in the dimensions of the artery wall when a pressure slightly above diastolic pressure is being applied by the cuff.

FIG. 4-c depicts a larger change in the dimensions of the artery wall when the cuff exerts a pressure greater than the pressure exerted by the cuff in FIG. 4-b.

FIG. 4-d depicts the maximum change in the dimensions of the artery wall when the cuff exerts a pressure on the artery equal to the means arterial pressure.

FIG. 4-e depicts a change in artery dimensions smaller than that in FIG. 4-d when the pressure exerted on the artery by the cuff is increased above mean arterial pressure.

FIG. 4-f depicts no change in artery dimensions because the pressure exerted on the artery by the cuff is so great that the heart cannot force the artery open at any point in its pumping cycle.

FIG. 5-a is a plot of three blood pressure pulse wave shapes for three beats of the heart.

FIG. 5-b is a plot of the amplitude of the dynamic component of the distal cuff pressure versus the magnitude of the static component of the distal cuff pressure.

FIG. 5-c is table of variables and their definitions.

FIG. 6-a is a plot showing the decline of the amplitude of the dynamic component of distal cuff pressure versus the increase in static proximal cuff pressure (when static distal cuff pressure is held constant near the mean arterial pressure).

FIG. 6-b is a plot showing rise and the subsequent decline of the amplitude of the dynamic component of distal cuff pressure versus the increase in static proximal cuff pressure (when static distal pressure is held constant below the mean arterial pressure).

FIG. 7 is a plot of the static proximal and distal cuff pressures throughout the monitoring process.

DETAILED DESCRIPTION OF THE PREFERRED EMBODIMENT

Figure 2A:
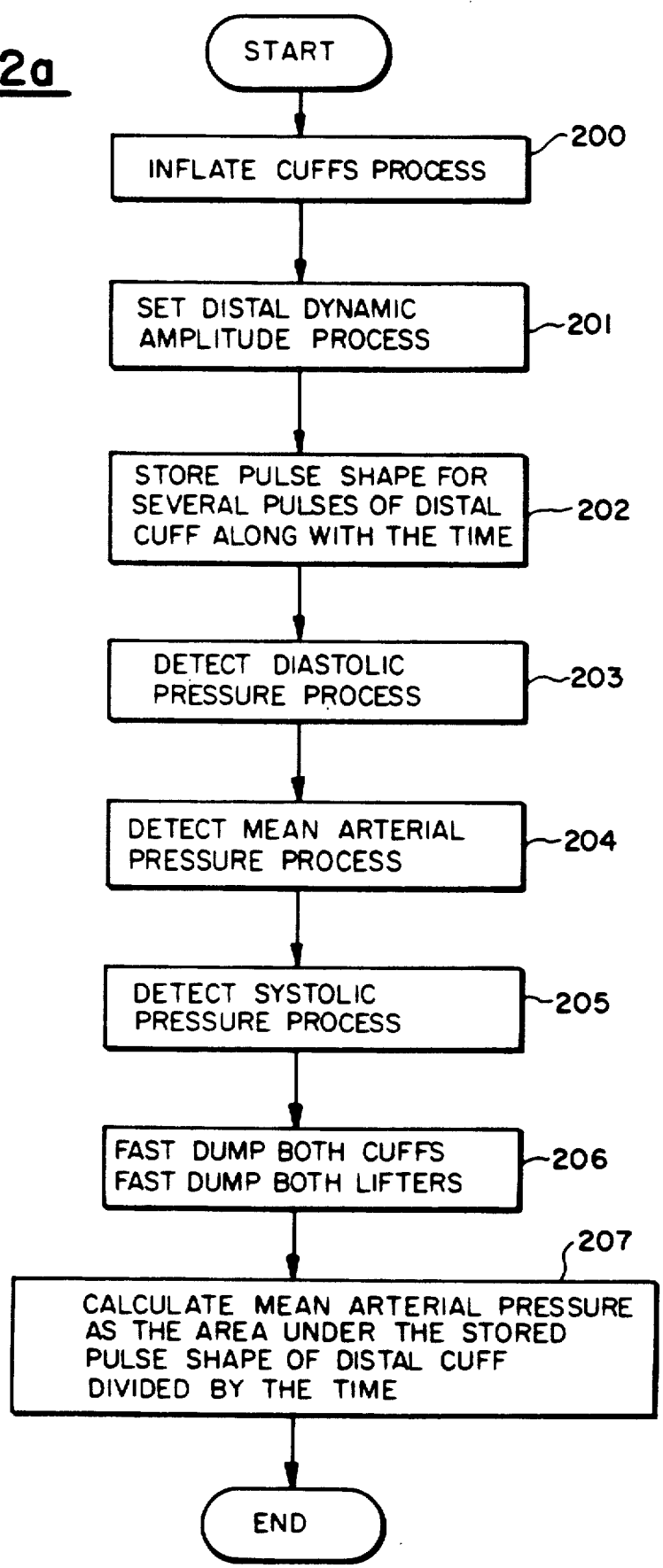
FIG. 2a is a general flowchart of a blood pressure measurement cycle.

A first embodiment will now be described. The embodiment uses two lifter assemblies (FIG. 1). The one nearer the heart will be referred to as the proximal lifter assembly and the other farther from the heart will be referred to as the distal lifter assembly. Each lifter assembly is mounted on shafts 1 using linear ball bushings 100 or some other means to reduce friction and noise. In the top of the lifter assembly is a cuff support cavity 2. The cuff support cavity 2 can be "V" shaped, "U" shaped, or parabolic shaped. The cuff support cavities 2 can also have a horizontal bracket 3 attached to the top of the opening (FIG. 1-A), attaching the cuff 6 in such a manner as to allow the inflation of the cuff 6 to create a sling around the finger. This will give contact between the cuff 6 and the finger 10 in excess of 180 degrees.

In the finger 10, the main arteries 4 run one on each side and under the bone structure 5 as shown in FIG. 1-B. The arteries 4 are bisected by a line running 30 degrees downward from the horizontal and approximately through the center of the finger 10. The cuff 6 is placed across the arteries 4 with each side of the cuff 6 being perpendicular to the center line that bisects the artery 4. The cuff 6 is a one piece device with a stem 8 attached to the center of the side in contact with the cavity 2.

The lifter cavity 2 in the preferred embodiment is "V" shaped and the "V" has an opening of approximately 60 degrees. The cuff 6 rests against the sides of the "V" shaped cavity 2 with the stem 8 extending downward, which gives the appearance of a "Y" shape where the stem 8 creates the base of the "Y" and the cuff 6 acts as two pads, one resting under each artery 4 of the finger.

The human finger 10 varies in size and location of the arteries 4; therefore, the cavity 2 must have some ability to wrap around the finger 10. This can be accomplished by the volume of air in the cuff 6 allowing the finger 10 to indent the cuff 6. The "U", parabolic, and sling shaped cuff cavities 2 can allow for a larger cuff 6 to artery 4 contact area. In all cases, the cuff 6 does not completely encircle the finger 10 which reduces the number of air pockets and wrinkles in the cuff 6, reducing the artifact. Also, by reducing the cuff volume, the ratio between the volume of air in the cuff 6 to the volume of blood in the artery 4 is reduced, which increases the gain of the system.

A small manifold 9 is connected to the cuff 6 using the stem 8 on the bottom side of the cuff 6. The manifold 9 is positioned under the cuff cavity 2 and attached to the cuff lifter 7. A pressure sensor 11 and input valve 12 are also attached to the cuff manifold 9. The second port of the input valve 12 is connected by air-tight fittings and a tubular member to a buffer, tank 13 (FIG. 2). Since the manifold 9 (FIG. 1) is small and the volume between the cuff 6 and the valve 12 is very small, the cuff 6 to arterial 4 volume ratio is kept very small.

A lifter bladder 14 is mounted under each lifter 7. Each lifter bladder 14 has one port which is connected via a tubular connection to a valve 15a and 15b (FIG. 2). The second port of the valve is connected to the buffer tank 13. The buffer tank 13 is provided to reduce turbulence and slow the flow rate to the distal cuff 6a, proximal cuff 6b, distal lifter bladder 14a and the proximal lifter bladder 14b. Also attached to the buffer tank 13 by air-tight connections is a dump valve 16 with the second port open to the atmosphere. The dump valve 16 is used to remove the air from the system at the end of the cycle.

A three way (slow dump) valve 17 is attached to the buffer tank 13 using another tubular member with air-tight fittings connected to the common port of the valve 17. To the normally open port of the valve 17 a fixed orifice 18 is connected which is vented to atmosphere. The normally closed port of the valve 17 has a fixed orifice 19 that is connected to a (T) fitting 20. A second port of the (T) fitting 20 is connected to a fast/slow valve 29 which is connected to the buffer tank 13. The fast/slow valve 29 is used to bypass the fixed orifice 19, which gives a path for fluid to go directly to the buffer tank 13, rapidly increasing the pressure in the buffer tank 13. The third port of the (T) fitting 20 is connected via a tubular member to another fixed orifice 21 which is connected to a stabilization tank 22. The stabilization tank 22 has a port connected by a tubular member to a pump 23.

The shafts 1 (FIG. 1) attached to the cuff lifter 7 are supported by a base plate. The base plate is part of a housing for the handset system. In addition to the base plate, the housing consists of two sides; a front and back. The housing can be made as one unit or in parts. The housing top 24 is used to support finger stops 25. One finger stop 25 is mounted above each cuff 6. The stops can be fix-mounted or mounted so a slight upward movement is necessary when the finger contacts the stop. A proximity sensor 26 limit switch or photocell can be used to detect the motion of the finger stop 25. When a fixed position finger stop 25 is used, a slight increase in cuff 6 pressure is used to detect the finger 10 being in contact with the finger stop 25. The preferred embodiment uses the slight increase in cuff 6 pressure method to detect finger 10 contact with the finger stop 25.

The microcomputer 26 controls distal cuff valve 12a, proximal cuff valve 12b, distal lifter valve 15a, proximal lifter valve 15b, dump valve 16, slow dump valve 17, fast/slow valve 21, and pump 23 which runs for a fixed amount of time.

METHOD ONE

In general operation, both proximal and distal cuffs are inflated until they press against the finger with a predetermined pressure (FIG. 2a step 200).

Distal lifters then further increase pressure exerted on the finger by the distal cuff. The distal lifter is set so that the amplitude of the dynamic distal pressure is either below, at, or above its maximum. The shape of the pulse sensed in the distal cuff is then recorded at step 202.

The proximal lifter then increases the pressure on the finger and the diastolic pressure is read at step 203. The proximal lifter further increases the pressure on the finger and the mean arterial pressure is read at step 204. The proximal lifter still further increases the pressure on the finger and the systolic pressure is read at step 205.

Both cuffs are deflated and the finger can be removed from the handset at step 206. Calculations are then performed on the data stored at step 207.

Figure 2B:
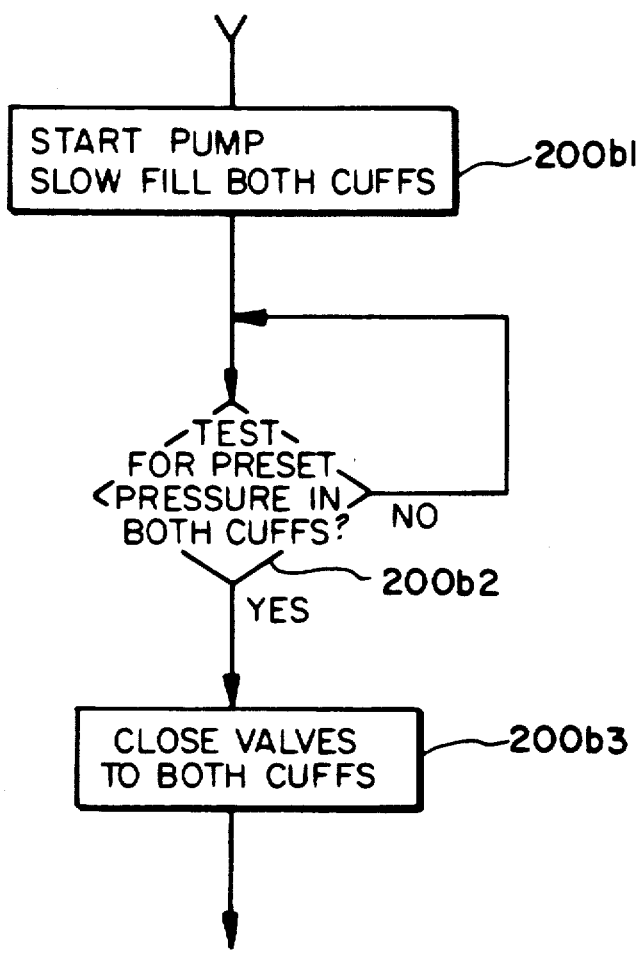
Figure 2C:
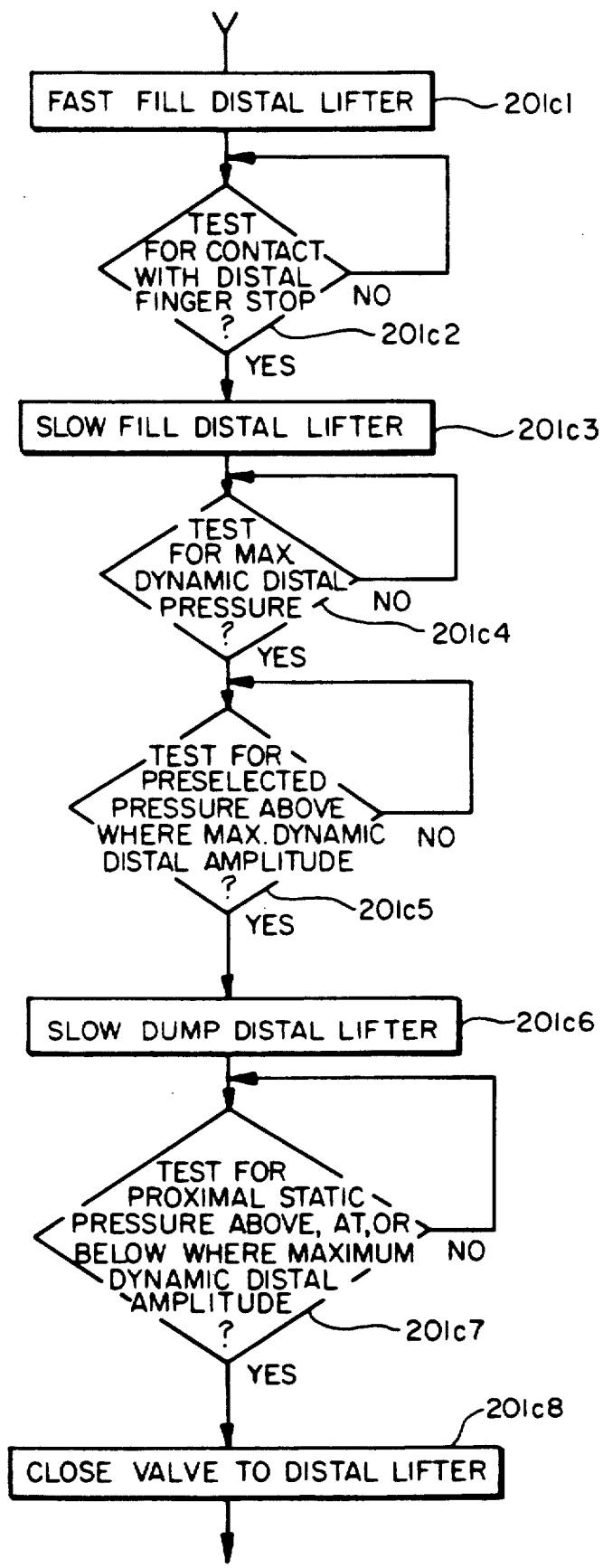
Figure 2E:
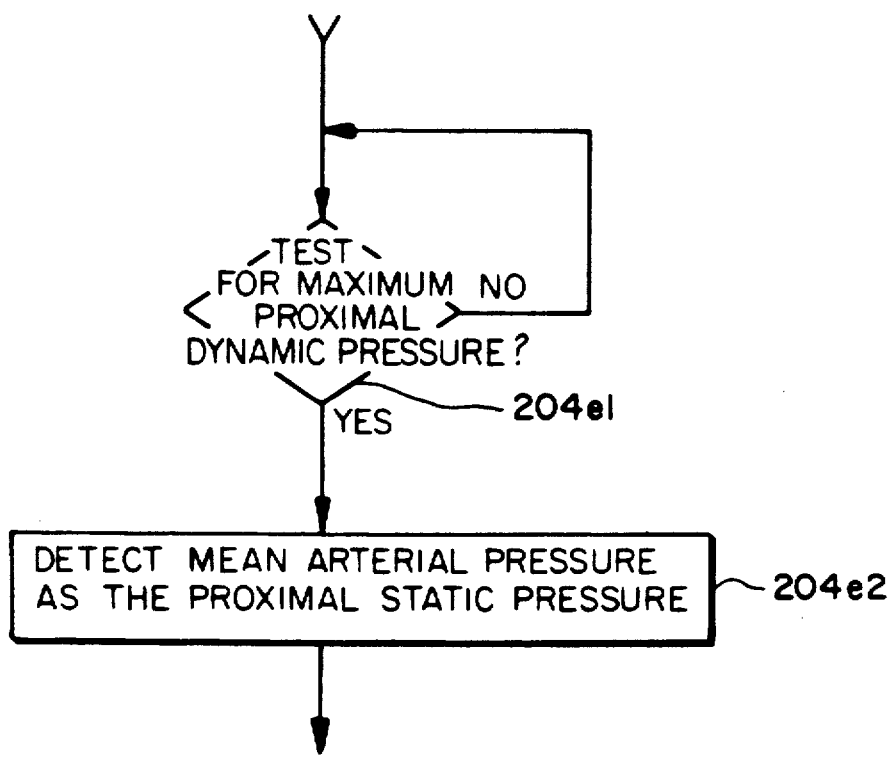
FIG. 2e is a flowchart of the Detect Mean Arterial Pressure Process of the general flowchart of FIG. 2a as used in methods one and two.
Figure 3:
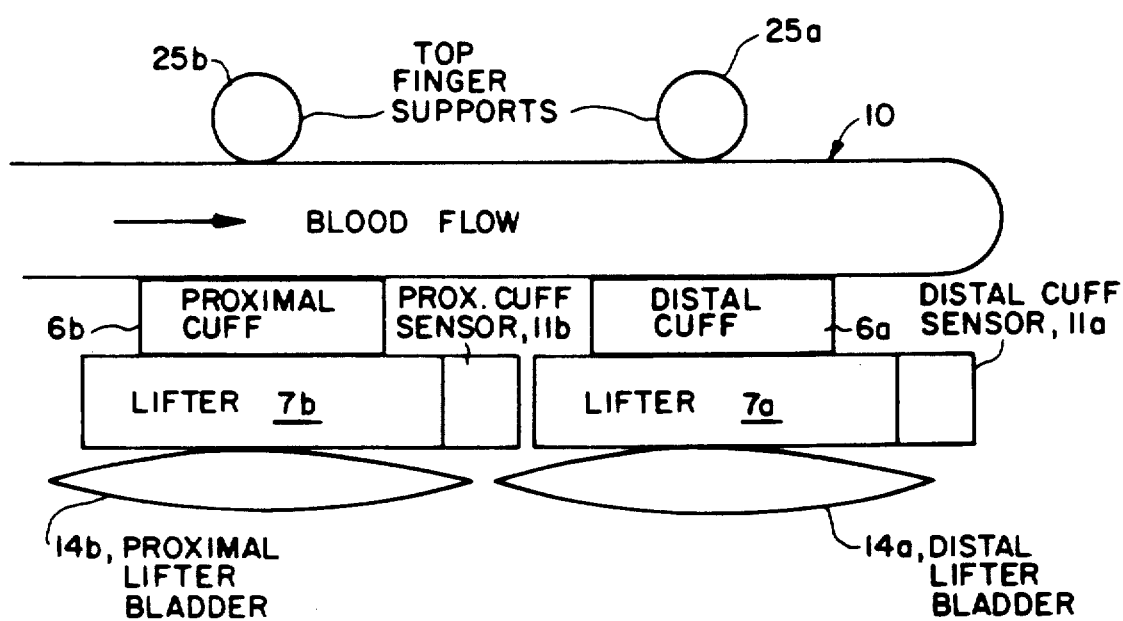
FIG. 3 is a diagram which depicts blood flow in an artery being affected by the proximal and the distal bladder-lifter-sensor-cuff-stop assembly.

More specifically, in method one, a finger 10 is placed in the handset with proximal cuff 6b and distal cuff 6a in contact with finger 10 (FIG. 3). When the cycle is started, microcomputer 26 activates pump 23 and closes distal lifter valve 15a, proximal lifter valve 15b, dump valve 16, and fast/slow valve 29 (FIG. 2) (FIG. 2b reference 200b1). Slow dump valve 17 is set to allow flow through fixed orifice 19 to the buffer tank 13. Pump 23 runs for a fixed amount of time. Air passes from pump 23 to stabilization tank 22 which stores the air and dampens some of the turbulence generated by pump 23. The air then passes through fixed orifice 21 which retards the flow rate and further reduces the pump 23 turbulence. Then the flow passes through second fixed orifice 19, slow dump valve 17, and to buffer tank 13.

Air continues through distal cuff valve 12a, through distal cuff manifold 9a, and inflates distal cuff 6a. Simultaneously, air flows through proximal cuff valve 12b, through proximal cuff manifold 9b, and inflates proximal cuff 6b at step 200b1. Pressure sensor 11a is mounted in the distal manifold 9a and a second pressure sensor 11b is mounted in the proximal manifold 9b.

When a preset pressure is attained in each cuff 6a and 6b as tested in step 200b2, microcomputer 26 closes the corresponding valve 12a and 12b. If the pressure goes over the predetermined value, slow dump valve 17 is deenergized, allowing flow from buffer tank 13 to the atmosphere. The valve controlling the over pressure cuff will open, allowing the cuff to be bled into buffer tank 13 and to the atmosphere.

Valves 12a and 12b remain closed throughout the remainder of the measuring cycle. This provides for a constant air mass and eliminates any turbulence created by movement of air in or out of cuffs 6a and 6b. In the prior art, a cuff which completely encircled the limb was inflated to exert a pressure on the limb of the body. Therefore, turbulence was a source of error.

Distal lifter valve 15a is opened and fast/slow valve 29 is opened to allow rapid inflation of distal lifter bladder 14a (FIG. 3). This causes a rapid rise in distal lifter 7a at step 200c1. When the finger 10 contacts top finger stop 25a, a slight increase in pressure is sensed on distal cuff sensor 11a at step 200c2 and fast/slow valve 29 (FIG. 2) is closed preventing further rapid flow into the buffer tank.

Figure 4A:
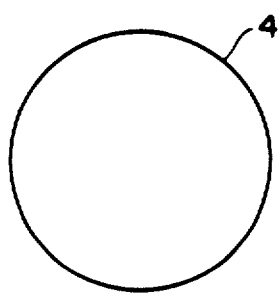
FIGS. 4-a through 4-f depict the changes in artery wall dimensions due to increasing cuff pressures being applied to the artery.
Figure 4B:
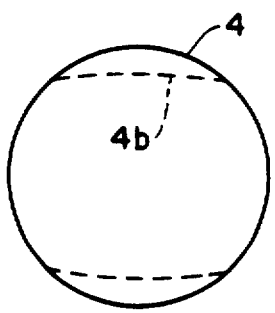
Figure 4C:
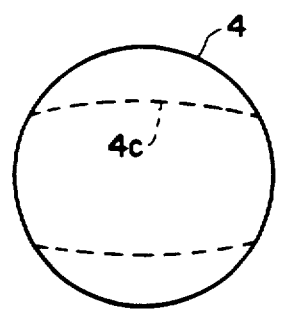
Figure 4D:
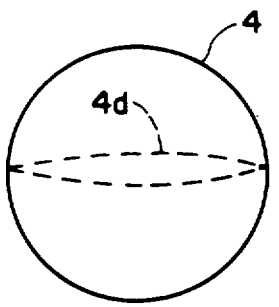
Figure 4E:
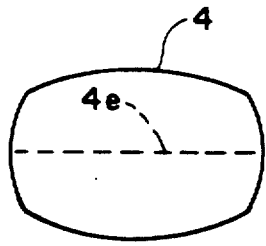

Flow still continues at step 200c3 through fixed orifice 19, to buffer tank 13, and to the distal lifter bladder 14a. Distal lifter 7a (FIG. 3) continues to rise but at a slower rate. Distal cuff sensor 11a (FIG. 2) produces a signal that is sent to microcomputer 26. The signal has both a static and a dynamic component. The static component is due to lifter 7a pushing distal pad 6a against the finger 10. The dynamic signal component is produced by the pulsation of blood through the arteries 4 (FIG. 1) with the cuff 6a in contact with the arteries 4. Even though no restriction of the arterial (FIG. 4A)

walls is present, signals are detected by the vibration of the walls 4 when blood passes through them.

The distal cuff signal is low pass filtered and digitally sampled by the microcomputer 26 under program control through an A/D converter to obtain a measure of the distal cuff 6a static pressure. The signal is also band pass filtered and amplified to obtain a measure of the distal cuff 6a dynamic pressure. The signal is zero referenced such that by the beginning of the systolic portion of each pulse, the signal has returned to zero volts. The signal is digitally sampled by the microcomputer under program control through an A/D converter. The maximum value attained by the signal is a true representation of the arterial systolic rise of the blood pressure pulse. The prior art uses a signal equivalent to a derivative of the pressure pulse. Because this method isolates the rate of change in slope, the derivative method has a tendency to amplify artifacts.

The dynamic signal amplitude is constantly being sampled. When the gain reaches a predetermined percentage of full scale deflection, system amplification is adjusted. The amplification can be increased or decreased as needed. The system can operate over a total gain ratio of approximately 50 to 1 accommodating a wide range of dynamic cuff 6a pressure amplitudes between subjects, without requiring the use of a very high resolution A/D converter (about 16 bits.) To be able to set the span of the A/D converter, a digital to analog converter (DAC) is used to produce a reference voltage. A DAC can also set an offset voltage for the A/D converter. The analog gain of the system is controlled by microcomputer 26 when it sets the DAC output voltages. If the limits of the electronics need adjusting the overall gain can also be varied by the amount of air placed in the cuff 6a. Varying the cuff 6a mass will change the overall system gain which affects the amount of amplification.

With the external pressure applied to arteries 4 being less than the diastolic pressure (FIG. 4A), the arterial walls 4 experience no restriction. Deflection of the arterial walls 4 occurs when the cuff 6a pressure is greater than the diastolic pressure and less than the systolic pressure. During each pulse cycle, the arterial walls 4 deflects when the pressure within the arteries 4 falls below the cuff 6a pressure. Therefore, when the cuff 6a pressure just exceeds the diastolic pressure, a slight deflection of the arteries 4b will occur during each pulse cycle. The deflection only occurs in the part of the pulse cycle (FIG. 5a) when the cuff 6a pressure is greater than the arterial 4 pressure (FIG. 4). When the pressure exerted on the arterial walls 4 by the cuff 6a increases, the deflection of the arterial walls 4 becomes greater and the time duration of the deflection cycle is greater 4c.

As the pressure exerted on the arterial walls 4 continues to increase, the pressure reaches the point of maximum deflection of the arterial walls 4d. This point occurs at the mean arterial pressure 28 (FIG. 5b). As the deflection of the arterial walls 4 occurs, the pulse is transmitted by the distal cuff 6a to the pressure sensor 11a. For each pulse the entire blood pressure wave shape is present (FIG. 5a) and the microcomputer 26 needs to retain only the peak value of the dynamic pulse signal which represents the electrical equivalent of the systolic pressure. The signal is passed through a peak hold circuit which retains the maximum value of the dynamic signal amplitude for each pulse. The microcomputer 26 operating under program control is digitally sampling the signal several times per second to obtain a measure of the distal cuff 6a peak amplitude per pulse at step 200c4. The microcomputer 26 operating under program control resets the peak hold circuit each time a pulse cycle is complete. The microcomputer 26 stores the time, the cuff 6a static pressure and the cuff 6a pulse peak value for each pulse.

As the distal static cuff 6a pressure rises above the mean arterial pressure 28 (FIG. 5b), the pulse peak dynamic signal amplitude per cycle declines. Microcomputer 26 operating under program control continues the process until some preselected reduction in pulse peak dynamic signal amplitude 29 occurs at step 200c5. This normally occurs at a distal static pressure that is approximately 10 mmHg above the static pressure where maximum pulse peak dynamic signal amplitude 28 occurred.

Once the distal dynamic signal amplitude exceeds its maximum peak value and the static pressure is exceeded by the selected amount, slow dump valve 17 (FIG. 2) deactivates which closes the path through fixed orifice 19 and opens a path through fixed orifice 18 which is open to atmosphere. Buffer tank 13 now slowly vents to the atmosphere and distal lifter valve 15a remains open so that distal lifter bladder 14a also slowly vents to the atmosphere at step 200c6. At step 200c7, venting continues until the volume of air in the distal lifter bladder 14a is reduced enough to lower the pressure on distal cuff 6a to the static pressure which corresponded to the maximum dynamic signal amplitude 28.

When the desired static pressure is reached, distal lifter valve 15a is closed at step 200c8. Slow dump valve 17 is energized to prevent flow through fixed orifice 18 and re-establish flow through fixed orifice 19. At this point, distal pad 6a is at a constant static pressure and volume. The only changes affecting distal pad 6a and pressure sensor 11a are the dynamic pulses which are now rising to maximum dynamic amplitude 28 with each beat of the heart. The predominate dynamic signal amplitude pulses come from the blood pulsation through the arteries 4.

The system is held steady for a predetermined number of pulses. Microcomputer 26 collects the data to generate a pulse shape curve complete with the dicrotic notch at step 202. A small sine wave which represents the respiratory pattern is also evident along the pulse peaks.

The distal cuff signal is band pass filtered, amplified, and digitally sampled by microcomputer 26 under program control through an A/D converter to obtain a measure of the pulse shape. The signal is also band pass filtered, amplified, clipped, and digitally sampled through an A/D converter by microcomputer 26 under program control. The time period of the variation in amplitude of the peaks in this signal is representative of the respiratory rate. Collecting several respiratory peaks and plotting them against time yields a respiratory cycle pattern. Accurate measurement of the pulse shape curve and the respiratory cycle are possible due to the small cuff 6a/artery 4 volume ratio.

In a standard arm cuff, the volume of air in the cuff can be as high as 400 times as great as the volume of the artery. With large ratios it is difficult to obtain enough resolution to detect small changes in the pulse amplitude. Often in arm cuff systems, the plumbing between the cuff and the sensor is several feet long. The signal is dampened as it travels through the length of tubing. This travel also decreases the sensitivity at the sensor.

In the preferred embodiment, the system is held in a steady state at the maximum distal cuff 6a dynamic signal amplitude 28. This is also the point when maximum arterial movement occurs (FIG. 4D) which allows for the maximum deflection of the system. Therefore, more signal detail is available for presentation.

Pressure sensor 6b attached to the proximal pad via proximal pad manifold 9b also sends signals to microcomputer 26. These signals can be calibrated to cuff 6b pressure. The signal is low pass filtered and digitally sampled by microcomputer 26 under program control through an A/D converter to obtain a measure of the proximal cuff 6b static pressure. In addition, the signal is band pass filtered, amplified, and digitally sampled by microcomputer 26 under program control through an A/D converter to obtain a measure of the proximal cuff 6b dynamic signal. The pressure of each pulse starts rising at the diastolic pressure 30 and rises until the systolic pressure peak value 31 is obtained (FIG. 5a); then the fall in blood pressure starts and continues past the dicrotic notch 32 and returns to the diastolic pressure 30 where the cycle starts over. Accordingly, the pressure sensor is zero referenced such that by the beginning of the systolic portion of each pulse, the signal has returned to zero volts. The maximum value obtained by the signal is a true representation of the actual systolic rise of the blood pressure pulse. By adjusting signal gain, microcomputer 26 automatically adjusts the amplitudes of the proximal signal and the distal signal. Similar to the distal cuff 6a process, this allows the proximal cuff 6b dynamic signal to operate over a total system gain ratio of approximately 50 to 1, accommodating the wide range of dynamic cuff pressure amplitudes between subjects without requiring the use of a very high resolution A/D converter (about 16 bits). The proximal signal is passed through a peak hold circuit which retains the maximum value of each pulse until reset by the microcomputer 26 under program control.

Therefore, the signal can be digitally sampled by the microcomputer 26 through an A/D converter to obtain a measure of the proximal cuff 6b pulse peak amplitude. The primary purpose of the peak hold circuit is to allow use of an inexpensive microcomputer 26 with an effective sampling rate less than 100 hertz.

At this point in the blood pressure measurement, distal cuff 6a pressure is stable and dynamic signals of approximately equal value 28 (FIG. 6a) are being sent to microcomputer 26. The pressure being exerted on the proximal artery 4 by the cuff 6b is, however, minimal.

Proximal lifter valve 15b is now opened and the fast/slow valve 29 is activated at step 203d1 of FIG. 2d, allowing air to bypass the fixed orifice 19 and rapidly fill the buffer tank 13 which in turn rapidly inflates the proximal lifter bladder 14b. The proximal lifter 7b rises which in turn raises the finger 10 which contacts the upper finger stop 25. The finger stop 25 can be manufactured to allow a slight upward movement which can be detected by a limit, proximity or photo switch. In the preferred embodiment, a slight increase in cuff 6b pressure sends a signal to the microcomputer 26 to indicate the finger 10 has contacted the finger stop 25 at step 203d2.

Now microcomputer 26 deactivates the fast/slow valve 29 which limits the flow to a path through fixed orifice 19 at step 203d3 and through slow/dump valve 17 which is set to allow flow to buffer tank 13. Proximal lifter valve 15b remains open throughout the remainder of the run. Proximal lifter 7b is now rising slowly, placing more pressure on proximal pad 6b and in turn the limb arteries 4. For each rise and fall of the blood pressure cycle, microcomputer 26 reads and saves the time, distal cuff 6a static pressure, distal pulse peak amplitude, proximal cuff 6b static pressure, and proximal pulse peak amplitude.

Maximum peak amplitude oscillations 28 are still occurring on the distal cuff (FIG. 6-A). As the proximal cuff 6b pressure exceeds the diastolic pressure, the flow through the arteries 4 at the point of the proximal cuff 6b is slightly reduced. Flow is reduced during the portion of the pulse cycle (FIG. 5a) that the cuff pressure is above the internal arterial pressure. This is a small amount just as the cuff 6b passes the diastolic pressure. The amount increases as the cuff 6b pressure increases (FIGS. 4a–4f). Now the arterial walls 4 of the distal cuff 6a are seeing a different pressure so the amplitude of the distal cuff 6a oscillations decrease because the internal arterial pressure has been reduced. The static pressure on the proximal cuff 6b is great enough to create a partial restriction of the artery 4, therefore reducing the downstream pressure, which causes a reduction in the arterial wall 4 movement and in turn reduces signal amplitude on the distal sensor 11a.

When the peak dynamic signal amplitude from the distal trace starts to become smaller at step 203d4, the diastolic pressure (D) is read as the static pressure on the proximal cuff (FIG. 6A) at step 203d5.

Also when the diastolic pressure is crossed in the proximal cuff 6b, the pressure difference between the two cuffs drops. This causes a reduction in the amplitude of the dicrotic notch 32 on the distal trace. Simultaneously recording the static pressure on the proximal cuff 6b gives the diastolic pressure.

As the proximal cuff 6b pressure continues to increase, the movement of the arterial walls continues to increase. When the arterial walls 4 move through maximum travel, maximum oscillation occurs on the proximal cuff 6b. This maximum oscillation point at step 204e1 of FIG. 2e and 2f and on the proximal trace corresponds to the mean arterial pressure (MAP) when the proper cuff volume and width are maintained (FIG. 6-A) at step 204e2.

The pressure on the proximal cuff 6b continues to increase. The arterial walls 4 come into contact and seal (FIG. 4E), which permits flow for a only a portion of the pulse cycle. As the proximal cuff 6b pressure continues to rise, the walls 4 stay closed for a larger portion of each pulse cycle. As the arterial walls 4 contact time increases, the time remaining for pulsation of the walls is reduced; therefore, the walls 4 travel through less distance with each pulse cycle. With smaller arterial wall 4 travel the amplitude of the dynamic signal in the proximal cuff 6b continues to decline (FIG. 6A). The dynamic signal amplitude on the distal cuff 6a has been declining since the diastolic pressure (D) was recorded. As the proximal lifter bladder 14b continues to increase in pressure causing an increase in the proximal cuff 6b pressure, the pressure on the arterial walls 4 under the proximal cuff 6b continues to increase. Pressure between the cuffs continues to decrease. The pressure on the proximal cuff 6b continues to increase until no flow is passing through the arteries 4.

At this point, the amplitude of the dynamic signal of the distal cuff 6a reduces to a minimum value and remains constant at step 205g1 of FIG. 2g. Systolic pressure (S) is indicated by the static pressure in proximal cuff 6b when the minimum distal dynamic amplitude is first achieved at step 205g2.

The cycle is terminated after the minimum amplitude of the oscillation values of the distal sensor 11a are recorded for some set time. When the run is terminated, proximal lifter valve 15b is closed, distal lifter valve 15a remains closed, and dump valve 16 and slow dump valve 17 are opened to the atmosphere. Fast/slow valve 29 is deenergized allowing fast flow to buffer tank 13. Stabilization tank 22 bleeds through fixed orifice 21 to buffer tank 13 and to the atmosphere. When the pressure inside stabilization tank 22 has decreased, distal cuff valve 6a, proximal cuff valve 6b, distal lifter valve 15a, and proximal lifter valve 15b are opened (FIG. 2a reference 206). After a few seconds, the finger 10 can be removed from the unit.

From the pulse shape curve (FIG. 5a) generated and stored, microcomputer 26 calculates the area under the curve 34 at step 207. The curve is relative voltage values and not calibrated in pressure. Since the peak of the curve occurs at systolic pressure 31 and the base of the curve occurs at diastolic pressure 30, the difference between the two values is a voltage value proportional to the difference between systolic (S) and diastolic (D) pressures.

Therefore, a value for the expression S-D is obtained. By definition, the mean arterial pressure (MAP) is the area under the pressure curve divided by time (FIG. 5-C) at step 207. By dividing the area under the crossed portion of curve 35 by time, the expression MAP-D is obtained. A (K) factor can also be calculated according to the equation K=(MAP-D)/(S-D). (see FIG. 5-C)

Because the mean arterial blood pressure (MAP), the diastolic blood pressure (D), and the systolic blood pressure (S) are already determined, these values can be substituted into the (K) factor equation. Because there are two ways of obtaining the (K) factor (FIG. 5-C), a relative reliability factor can be obtained. If the data is consistently out of limits, microcomputer 26 can take the unit out of service.

During the run, distal cuff 6a pressure is held constant and proximal cuff 6b pressure increases at a steady rate and the pressure values are retained by the microcomputer 26. A plot of the distal cuff 6a pressure reveals a horizontal line 36 (FIG. 7). A plot of the proximal cuff 6b pressure reveals a line 37 that is approximately straight and slopes upward to the right. By analyzing the data, the microcomputer 26 can determine if the unit has problems and should be taken out of service.

METHOD TWO

The second method sets the static distal cuff pressure above the point where the dynamic distal signal amplitude was at maximum value 28. All the steps in FIGS. 2a-2g are the same for method one and method two except that steps 201c7 and 201c8 on FIG. 2c serve to set the static distal cuff pressure above the point where the dynamic distal signal amplitude was maximum.

The change in distal dynamic pressure being tested for in step 203d4 of FIG. 2d is a decrease in distal dynamic pressure just as it was in method one. The only difference is that method two detects a decrease from a distal dynamic pressure which was not the maximum. Method one detected a decrease from the maximum.

METHOD THREE

The third method sets the static distal cuff pressure below the pressure where the distal dynamic signal amplitude was at maximum value 28. Accordingly, when the pressure exerted on the artery by the proximal cuff is increased, the distal dynamic amplitude actually increases up to a maximum before it decreases down to its minimum. Therefore, the change being tested for in step 203d4 of FIG. 2d is an increase in distal dynamic pressure, not a decrease as it was in methods one and two.

Method three also includes additional steps 204f1 and 204f2 on FIG. 2f which are not included in methods one and two. Because method three involves the distal dynamic pressure increasing to its maximum amplitude when the proximal cuff pressure is increased, method three has two ways of measuring maximum dynamic pressure. In addition to detecting the maximum dynamic pressure (proximal) as a function of proximal static pressure in steps 203e1 and 203e2, the maximum dynamic pressure (distal) can be measured as a function of proximal static pressure in steps 204f1 and 204f2.

In more detail, the blood pressure measurement cycle is initiated by inflating both cuffs at step 200 as in methods one and two. At steps 201c7 and 201c8, the distal lifter sets the distal cuff pressure a predetermined amount below the pressure where maximum dynamic signal amplitude 28 occurs. The system is held steady for a predetermined number of pulses while microcomputer 26 collects data to store a pulse shape curve complete with the dicrotic notch at step 202.

The proximal lifter then increases the pressure at steps 203d1, 203d2, and 203d3. When the proximal cuff pressure exceeds the diastolic pressure (D), a slight deflection of the arterial wall 4 occurs at the proximal cuff 6b (FIG. 4-B) reducing the blood pressure in the distal arteries 4. Because the distal arteries 4 were oscillating with an externally applied static pressure below the value at which maximum dynamic signal amplitude 28 would be obtained, reducing the blood pressure in the arteries allows the distal cuff 6a to force the arterial wall more closed during each pulse as represented by 4c of FIG. 4c. Accordingly, a rise in the dynamic signal amplitude (D) on the distal cuff 6a (FIG. 6-B) is sensed at step 203d4. The proximal static pressure at which the rise in the distal dynamic signal amplitude occurs represents the diastolic pressure (D) at step 203d5.

When the pressure between the cuffs drops, a change in the amplitude of the dicrotic notch on the distal trace occurs. Simultaneously recording the static pressure on the proximal trace also gives the diastolic pressure (D).

As the proximal cuff pressure increases further, maximum distal dynamic signal amplitude is reached at step 204e1 and the mean arterial pressure (MAP) is read as the static proximal pressure at step 204e2. The maximum proximal dynamic signal is also reached at step 204f1 and the mean arterial pressure (MAP) is also read as the static proximal pressure (FIG. 6-B) at step 204f2. Since both the maximum distal and the maximum proximal dynamic signal yield the mean arterial pressure (MAP), both the maximum distal and the maximum proximal dynamic pressures must occur at the same time and pressure.

Figure 4F:
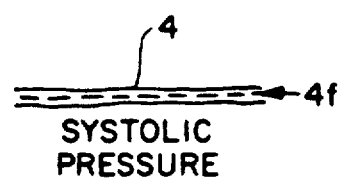

Next, when the pressure on the proximal cuff 6b continues to rise, arterial walls 4 come into contact and seal momentarily which prevents flow for part of the cycle (FIG. 4F). As the time that arterial walls 4 remain in contact increases, the time remaining for blood pulsation through the artery is reduced. The walls 4 travel through less distance with each pulse cycle. With smaller arterial wall travel, the amplitude of the proximal dynamic signal declines.

The dynamic distal signal amplitude also declines after the mean arterial pressure (MAP) is passed (FIG. 6-B). As proximal lifter bladder 14b continues to increase in pressure, blood flow through the arteries 4 decreases, dynamic distal amplitude reduces to a minimum value and remains constant at step 205g1 of FIG. 2g. The static proximal pressure where the minimum dynamic distal amplitude is first achieved indicates the systolic pressure (S) at step 205g2.

The (K) factor can also be calculated from the pulse shape curve as previously described. The (K) factors from the curve and the actual values can be compared to obtain a relative reliability factor. If the data is consistently out of tolerance the microcomputer 26 can take the unit out of service. Traces showing the static pressure on each cuff throughout the run can be plotted (FIG. 7). If the traces are out of limits, the unit can be taken out of service.

The blood pressure measurement is terminated as in methods one and two by retracting both lifters at step 206, deflating both cuffs at step 206, and analyzing the results of the meansurement at step 207.

We claim:

1. An automatic blood pressure measuring system for measuring a blood pressure in a blood vessel of a living body comprising:
   proximal cuff means, inflated to include a first fixed mass of air, for exerting a pressure at a first location on the blood vessel;
   proximal sensing means, coupled to said proximal cuff means, for sensing a pressure of said first fixed mass of air of said proximal cuff means and producing a proximal sensing means output signal indicative thereof;
   proximal lifting means for pressing said proximal cuff means against the blood vessel at said first location;
   distal cuff means, inflated to include a second fixed mass of air, for exerting a pressure on the blood vessel at a second location farther from the heart than said first location;
   distal sensing means, coupled to said distal cuff means, for sensing a pressure of said second fixed mass of air of said distal cuff means and producing a distal sensing means output signal indicative thereof;
   distal lifting means for pressing said distal cuff means against the blood vessel at said second location; and
   processing means for:
      controlling said proximal lifting means and said distal lifting means to press said proximal cuff means and said distal cuff means against the blood vessel when a blood pressure reading is desired;
      monitoring said proximal sensing means output signal and said distal sensing means output signal; and
      determining the blood pressure based on said proximal sensing means output signal and said distal sensing means output signal.

2. Apparatus of claim 1 further comprising:
   a proximal valve for introducing air into and releasing air from said proximal cuff means;
   a distal valve for introducing air into and releasing air from said distal cuff means; and
   a high pressure air source for inflating said proximal cuff means and said distal cuff means to said first and second fixed mass of air, respectively, through said proximal valve and said distal valve respectively.

3. Apparatus of claim 2 wherein said processing means is also for:
   controlling said proximal valve, said distal valve, and said high pressure air source, before measuring the blood pressure, such that said proximal cuff means and said distal cuff means are inflated with high pressure air from said high pressure air source until said proximal cuff means is filled with said first fixed mass of air and said distal cuff means is filled with said second fixed mass of air; and
   controlling said proximal valve and said distal valve after measuring the blood pressure has taken place such that said high pressure air is released from said proximal cuff means and said distal cuff means.

4. Apparatus of claim 1 wherein said processing means is also for:
   filtering said proximal sensing means output signal such that said pressure of said first mass of air is separated into a proximal static pressure and a proximal dynamic pressure;
   filtering said distal sensing means output signal such that said pressure of said second mass of air is separated into a distal static pressure and a distal dynamic pressure; and
   determining the blood pressure based on said proximal static pressure, said proximal dynamic pressure, said distal static pressure, and said distal dynamic pressure.

5. Apparatus of claim 4 wherein said processing means is also for:
   controlling said distal lifting means such that said distal dynamic pressure increases to a maximum and then decreases;
   monitoring said distal dynamic pressure and said distal static pressure to determine said maximum;
   fixing said distal lifting means such that said distal dynamic pressure remains substantially at said maximum;
   subsequent to said fixing step, controlling said proximal lifting means such that said proximal static pressure increases to a first diastolic pressure where said distal dynamic pressure decreases from said maximum;
   monitoring said distal dynamic pressure and said proximal static pressure to determine said first diastolic pressure;
   controlling said proximal lifting means such that said proximal static pressure increases to a mean arterial pressure where said proximal dynamic pressure increases to a maximum and then decreases;
   monitoring said proximal dynamic pressure and said proximal static pressure to determine said mean arterial pressure;
   controlling said proximal lifting means such that said proximal static pressure increases to a systolic pressure where said distal dynamic pressure decreases to a minimum; and
   monitoring said distal dynamic pressure and said proximal static pressure to determine said systolic pressure.

6. Apparatus of claim 5 wherein said processing means is also for:
   recording said distal sensing means output signal to reveal pressure pulses of individual heart beats;

calculating a first K value according to the following formula where S is the lowest recorded value of said distal sensing means output signal, D is the highest recorded value of said distal sensing means output signal, and MAP is the average of the recorded distal sensing means output signal over a heart beat:

$$K = (MAP-D)/(S-D);$$

calculating a second K value according to the following formula where S is said systolic pressure, D is said diastolic pressure, and MAP is said mean arterial pressure;

$$K = (MAP-D)/(S-D); \text{ and}$$

comparing said first K value and said second K value to determine a reliability factor for the blood pressure measurement.

7. Apparatus of claim 4 wherein said processing means is also for:
controlling said distal lifting means such that said distal dynamic pressure increases to a maximum and then decreases;
monitoring said distal dynamic pressure and said distal static pressure to determine said maximum;
fixing said distal lifting means such that said distal static pressure remains at a fixed value above said distal static pressure corresponding to said maximum;
subsequent to said fixing step, controlling said proximal lifting means such that said proximal static pressure increases to a diastolic pressure where said distal dynamic pressure decreases from said fixed value;
monitoring said distal dynamic pressure and said proximal static pressure to determine said diastolic pressure;
controlling said proximal lifting means such that said proximal static pressure increases to a mean arterial pressure where said proximal dynamic pressure increases to a maximum and then decreases;
monitoring said proximal dynamic pressure and said proximal static pressure to determine said mean arterial pressure;
controlling said proximal lifting means such that said proximal static pressure increases to a systolic pressure where said distal dynamic pressure decreases to a minimum; and
monitoring said distal dynamic pressure and said proximal static pressure to determine said systolic pressure.

8. Apparatus of claim 7 wherein said processing means is also for:
recording said distal sensing means output signal to reveal pressure pulses of individual heart beats;
calculating a first K value according to the following formula where S is the lowest recorded value of said distal sensing means output signal, D is the highest recorded value of said distal sensing means output signal, and MAP is the average of the recorded distal sensing means output signal over a heart beat:

$$K = (MAP-D)/(S-D);$$

calculating a second K value according to the following formula where S is said systolic pressure, D is said diastolic pressure, and MAP is said mean arterial pressure:

$$K = (MAP-D)/(S-D); \text{ and}$$

comparing said first K value and said second K value to determine a reliability factor for the blood pressure measurement.

9. Apparatus of claim 4 wherein said processing means is also for:
controlling said distal lifting means such that said distal dynamic pressure increases to a maximum and the decreases;
monitoring said distal dynamic pressure and said distal static pressure to determine said maximum;
fixing said distal lifting means such that said distal static pressure remains at a fixed value below said distal static pressure corresponding to said maximum;
subsequent to said fixing step, controlling said proximal lifting means such that said proximal static pressure increases to a diastolic pressure where said distal dynamic pressure increases from said fixed value;
monitoring said distal dynamic pressure and said proximal static pressure to determine said diastolic pressure;
controlling said proximal lifting means such that said proximal static pressure increases to a mean arterial pressure where said proximal dynamic pressure increases to a maximum and then decreases;
monitoring said proximal dynamic pressure and said proximal static pressure to determine said mean arterial pressure;
controlling said proximal lifting means such that said proximal static pressure increases to a systolic pressure where said distal dynamic pressure decreases to a minimum; and
monitoring said distal dynamic pressure and said proximal static pressure to determine said systolic pressure.

10. Apparatus of claim 9 wherein said processing means is also for:
controlling said proximal lifting means such that said proximal static pressure increases to another mean arterial pressure where said distal dynamic pressure increases to said maximum;
monitoring said distal dynamic pressure and said proximal static pressure to determine said another mean arterial pressure.

11. Apparatus of claim 9 wherein said processing means is also for:
recording said distal sensing means output signal to reveal pressure pulses of individual heart beats;
calculating a first K value according to the following formula where S is the lowest recorded value of said distal sensing means output signal, D is the highest recorded value of said distal sensing means output signal, and MAP is the average of the recorded distal sensing means output signal over a heart beat:

$$K = (MAP-D)/(S-D);$$

calculating a second K value according to the following formula where S is said systolic pressure, D is said diastolic pressure, and MAP is said mean arterial pressure:

$K = (MAP-D)/(S-D)$, and comparing said first K value and said second K value to determine a reliability factor for the blood pressure measurement.

12. Apparatus of claim 4 wherein said processing means is also for:
monitoring the amplitude envelope of said distal dynamic pressure to reveal periodic oscillations due to respiration; and
timing the period of said periodic oscillations of said amplitude envelope to determine a respiratory rate.

13. Apparatus of claim 4 wherein said processing means is also for:
monitoring the amplitude of said distal dynamic pressure to reveal pressure pulses of individual heart beats; and
timing the period of said pressure pulses to determine a pulse rate.

14. An apparatus for measuring a blood pressure in a blood vessel of a limb of a body comprising:
a cuff;
inflating means for inflating said cuff to a fixed mass of air before a measurement interval, and for sealing said fixed mass of air into said cuff throughout said measurement interval;
pressing means for pressing said cuff, after said sealing and during said measurement interval, to generate a pressure on the blood vessel;
sensing means coupled to said cuff, for sensing a pressure of said fixed mass of air of said cuff and for producing an output signal indicative thereof; and
calculating means for calculating a blood pressure based on said sensed pressure.

15. Apparatus of claim 14 wherein:
said cuff contacts less than the entire limb.

16. Apparatus of claim 14 wherein:
said cuff has a small volume compared with the volume of the blood vessel.

17. Apparatus of claim 14 further comprising:
limb stopping means, disposed on an opposite side of the limb from said cuff for forming a surface against which said pressure means presses the limb.

18. Apparatus of claim 17 further comprising:
a proximity sensor, coupled to said limb stopping means, for detecting when the limb is pressed against said limb stopping means.

19. An apparatus for measuring a blood pressure in a blood vessel of a limb of a body comprising:
cuff;
inflating means for inflating said cuff to a fixed mass of air;
pressing means for pressing said cuff, inflated to said fixed mass of air, to exert a pressure on the blood vessel;
sensing means, coupled to said cuff, for sensing a pressure of said fixed means of air of said cuff and for producing an output signal indicative thereof; and
calculating means for calculating a blood pressure on said sensed pressure, wherein said inflating means comprises:
a high pressure air source for producing high pressure air with minimal pressure variations; and
a buffer tank for receiving said high pressure air from said high pressure air source and muffling said variations in said air pressure.

20. An apparatus for measuring a blood pressure in a blood vessel of a limb of a body comprising:
cuff means;
inflating means for inflating said cuff means to a fixed mass of air, the inflating means comprising:
a high pressure air source for producing high pressure air with minimal pressure variations; and
a buffer tank for receiving said high pressure air from said high pressure air source and muffling said variations in said air pressure;
pressing means for pressing said cuff means, inflated to said fixed mass of air, to exert a pressure on the blood vessel, the pressing means including:
a lifter bladder for receiving said muffled high pressure air from said buffer tank and for expanding when said muffled high pressure air from said buffer tank is introduced thereinto;
a base plate, coupled to said lifter bladder, against which said lifter bladder presses to expand; and
a lifter for moving away from said base plate, the lifter being coupled to said lifter bladder on the side opposite said base plate such that expansion of said lifter bladder between said base plate and said lifter moves the lifter away from said base plate;
sensing means, coupled to said cuff means, for sensing a pressure of said fixed mass of air of said cuff means and for producing an output signal indicative thereof; and
calculating means for calculating a blood pressure on said sensed pressure.

21. A method of measuring blood pressure in a blood vessel, comprising the steps of:
applying a distal pressure to the blood vessel at a first location such that the blood vessel opens and closes the maximum amount possible with each beat of the heart;
subsequent to applying said distal pressure, applying a proximal pressure to the blood vessel at a second location on the blood vessel closer to the heart;
recording a diastolic pressure as a lowest value of said proximal pressure where said blood vessel at said first location opens and closes less than said maximum amount possible; and
recording a systolic pressure as a lowest value of said proximal pressure where said blood vessel at said first location remains closed during each beat of the heart.

22. The method of claim 21 further including the step of:
recording a mean arterial pressure as said distal pressure applied to the blood vessel at a first location where the blood vessel opens and closes the maximum amount possible on each beat of the heart.

23. A method of measuring blood pressure in a blood vessel comprising the steps of:
applying a distal pressure to the blood vessel at a first location such that the blood vessel opens and closes less than a maximum amount possible on each beat of the heart;
subsequent to applying said distal pressure, applying a proximal pressure to the blood vessel at a second location on the blood vessel closer to the heart;
recording diastolic pressure as the lowest value of said proximal pressure where the amount said blood vessel at said first location opens and closes changes;

recording systolic pressure as said the lowest value of said proximal pressure where said blood vessel at said first location remains closed during each beat of the heart;

24. The method of claim 23 further including the step of:

recording mean arterial pressure as said distal pressure applied to the blood vessel at a first location where the blood vessel opens and closes the maximum amount possible on each beat of the heart.

25. The method of claim 24 further including the step of:

recording mean arterial pressure as the proximal pressure where said blood vessel at said first location opens and closes the maximum amount possible on each beat of the heart.

* * * * *